US010709682B2

(12) United States Patent
Knipper-Breer et al.

(10) Patent No.: US 10,709,682 B2
(45) Date of Patent: Jul. 14, 2020

(54) TREATMENT OF TINNITUS THROUGH MODULATION OF CHLORIDE CO-TRANSPORTER NKCC1 IN THE AUDITORY SYSTEM

(71) Applicant: OTOLANUM AG, Zug (CH)

(72) Inventors: Marlies Knipper-Breer, Leinfelden-Echterdingen Stetten (DE); Luckas Ruettiger, Kusterdingen (DE)

(73) Assignee: Otolanum AG, Zug (CH)

( * ) Notice: Subject to any disclaimer, the term of this patent is extended or adjusted under 35 U.S.C. 154(b) by 0 days.

(21) Appl. No.: 15/869,929

(22) Filed: Jan. 12, 2018

(65) Prior Publication Data
US 2018/0360797 A1 Dec. 20, 2018

Related U.S. Application Data

(63) Continuation of application No. 15/166,359, filed on May 27, 2016, now abandoned, which is a continuation of application No. 14/364,050, filed as application No. PCT/EP2011/072480 on Dec. 12, 2011, now abandoned.

(51) Int. Cl.
| *A61K 31/341* | (2006.01) |
| *A61K 38/17* | (2006.01) |
| *A61K 31/18* | (2006.01) |
| *A61K 31/196* | (2006.01) |
| *A61K 31/382* | (2006.01) |
| *A61K 31/402* | (2006.01) |
| *A61K 31/41* | (2006.01) |
| *A61K 31/433* | (2006.01) |
| *A61K 31/44* | (2006.01) |
| *A61K 31/542* | (2006.01) |
| *A61K 31/549* | (2006.01) |
| *A61K 45/06* | (2006.01) |
| *A61K 31/713* | (2006.01) |
| *A61K 9/00* | (2006.01) |
| *C12N 15/113* | (2010.01) |
| *G01N 33/68* | (2006.01) |
| *G01N 33/50* | (2006.01) |

(52) U.S. Cl.
CPC .......... *A61K 31/341* (2013.01); *A61K 9/0046* (2013.01); *A61K 31/18* (2013.01); *A61K 31/196* (2013.01); *A61K 31/382* (2013.01); *A61K 31/402* (2013.01); *A61K 31/41* (2013.01); *A61K 31/433* (2013.01); *A61K 31/44* (2013.01); *A61K 31/542* (2013.01); *A61K 31/549* (2013.01); *A61K 31/713* (2013.01); *A61K 38/1709* (2013.01); *A61K 45/06* (2013.01); *C12N 15/1138* (2013.01); *G01N 33/502* (2013.01); *G01N 33/5058* (2013.01); *G01N 33/6872* (2013.01); *C12N 2310/11* (2013.01); *C12N 2310/12* (2013.01); *C12N 2310/14* (2013.01); *G01N 2500/04* (2013.01)

(58) Field of Classification Search
CPC .... A61K 31/18; A61K 31/196; A61K 31/341; A61K 31/382; A61K 31/402; A61K 31/41; A61K 31/433; A61K 31/44; A61K 31/542; A61K 31/549; A61K 31/713; A61K 9/0046; A61K 38/1709; A61K 45/06; G01N 33/502; G01N 33/5058; G01N 33/6872; G01N 2500/04; C12N 15/1138; C12N 2310/11; C12N 2310/12; C12N 2310/14
See application file for complete search history.

(56) References Cited

U.S. PATENT DOCUMENTS

| 3,254,124 A | 5/1966 | Stevens |
| 4,044,021 A * | 8/1977 | Hanifin, Jr. .......... C07D 233/46 514/870 |
| 4,954,486 A | 9/1990 | Guth |
| 5,421,818 A | 6/1995 | Arenberg |
| 5,474,529 A | 12/1995 | Arenberg |
| 5,476,446 A | 12/1995 | Arenberg |
| 5,770,559 A | 6/1998 | Manning et al. |
| 5,863,927 A | 1/1999 | Smith et al. |
| 6,017,961 A | 1/2000 | Flores et al. |
| 6,045,528 A | 4/2000 | Arenberg et al. |
| 6,066,652 A | 5/2000 | Zenner et al. |

(Continued)

FOREIGN PATENT DOCUMENTS

| DE | 2062620 | 7/1971 |
| DE | 10124953 | 12/2002 |

(Continued)

OTHER PUBLICATIONS

Bauer, C. A. et al., Behavioral model of chronic tinnitus in rats, Otolaryngol Head Neck Surg., Oct. 1999, 121(4):457-462.

(Continued)

*Primary Examiner* — Robert S Landsman
(74) *Attorney, Agent, or Firm* — Cooley LLP

(57) ABSTRACT

The present invention relates to the treatment or prevention of tinnitus. More precisely, the present invention relates to a compound modulating chloride co-transporter NKCC1 (chloride co-transporter modulator) for use in the treatment of tinnitus. In addition, the present invention concerns pharmaceutical compositions comprising such an NKCC1 chloride co-transporter modulator as an active agent, a method for the treatment or prevention of tinnitus by administering such a chloride co-transporter modulator, and a screening method for the identification and characterization of compounds capable of modulating chloride co-transporter NKCC1.

14 Claims, 3 Drawing Sheets

(56) References Cited

U.S. PATENT DOCUMENTS

| | | | |
|---|---|---|---|
| 6,120,484 | A | 9/2000 | Silverstein |
| 6,309,410 | B1 | 10/2001 | Kuzma et al. |
| 6,377,849 | B1 | 4/2002 | Lenarz et al. |
| 6,656,172 | B1 | 12/2003 | Hildebrand |
| 6,969,383 | B2 | 11/2005 | Hildebrand |
| 7,214,711 | B2 | 5/2007 | Hochman |
| 7,294,345 | B2 | 11/2007 | Haapakumpu et al. |
| 8,268,866 | B2 | 9/2012 | Guitton et al. |
| 8,507,525 | B2 | 8/2013 | Guitton et al. |
| 2002/0039995 | A1 | 4/2002 | Gao |
| 2002/0082554 | A1 | 6/2002 | Lenarz et al. |
| 2003/0082214 | A1 | 5/2003 | Williams et al. |
| 2003/0225116 | A1 | 12/2003 | Chizh et al. |
| 2004/0062819 | A1 | 4/2004 | Hildebrand |
| 2007/0021352 | A1 | 1/2007 | Anderson et al. |
| 2009/0246255 | A1 | 10/2009 | Meyer |
| 2012/0302554 | A1 | 11/2012 | Knipper-Breer et al. |

FOREIGN PATENT DOCUMENTS

| | | |
|---|---|---|
| EP | 1682149 | 12/2009 |
| GB | 1074927 | 7/1967 |
| GB | 1330878 | 9/1973 |
| JP | 2009-102330 A | 5/2009 |
| JP | 2011-231094 A | 11/2011 |
| WO | WO 1994/008599 | 4/1994 |
| WO | WO 1997/038698 | 10/1997 |
| WO | WO 1998/010757 | 3/1998 |
| WO | WO 2001/089505 | 11/2001 |
| WO | WO 2001/098265 | 12/2001 |
| WO | WO 2002/015907 | 2/2002 |
| WO | WO 2002/020481 | 3/2002 |
| WO | WO 2004/022069 | 3/2004 |
| WO | WO 2004/043902 | 5/2004 |
| WO | WO 2004/064912 | 8/2004 |
| WO | WO 2004/101072 | 11/2004 |
| WO | WO 2005/073237 | 8/2005 |
| WO | WO 2005/094799 | 10/2005 |
| WO | WO 2010/085352 | 7/2010 |

OTHER PUBLICATIONS

Binder, D. K. et al. (eds.), The role of BDNF in epilepsy and other diseases of the mature nervous system, Chapter 3 in Recent Advances in Epilepsy Research, Plenum Publishers, 2004, pp. 34-56.
Bobys, H., Phantom pain: Location and causation, 2002, Biology 202, 2 pages.
Casey, W. F. et al., Spinal anesthesia—a practical guide, practical procedures, Issue 12, 2000, Article 8, 5 pages.
Chandrasekhar, S. S. et al., Dexamethasone pharmacokinetics in the inner ear: comparison of route of administration and use of facilitating agents, Otolaryngol Head Neck Surg., Apr. 2000, 122(4):521-528.
Chen, Z et al., Acute treatment of noise trauma with local caroverine application in the guinea pig, Acta Otolaryngol., Oct. 2003, 123(8):905-909.
Chen, Z et al., Pharmacokinetics of caroverine in the inner ear and its effects on cochlear function after systemic and local administrations in Guinea pigs, Audiol Neurootol, Jan.-Feb. 2003, 8(1):49-56.
Ciocon, J. O. et al., Does oxazepam offer relief of tinnitus or alter it to a non-troublesome functional level in the elderly?, Journal of the American Geriatrics Society, 1997, 45(9):122.
Clark, M. R. et al., Perspectives on pain and depression, Adv Psychosom Med., 2004, 25:1-27.
Database WPI Week 200169, Derwent Publications Ltd, XP002401093, 3 pages.
Denk, D. M. et al., Caroverine in tinnitus treatment. A placebo-controlled blind study, Acta Otolaryngol., Nov. 1997, 117(6):825-830.
Dirig, D. M. et al., Intrathecal baclofen and muscimol, but not midazolam, are antinociceptive using the rat-formalin model, J Pharmacol Exp Ther., Oct. 1995, 275(1):219-227.
Dobie, R. A., A review of randomized clinical trials in tinnitus, The Laryngoscope, Aug. 1999, 109(8):1202-1210.
Dodson, K. M. et al., Intratympanic perfusion for the treatment of tinnitus, Otolaryngol Clin North Am., Oct. 2004, 37(5):991-1000.
Domeisen, H. et al., Caroverine in tinnitus treatment, Acta Otolaryngol. (Stockh), Jul. 1998, 118(4):606-607.
Eaton, M., Common animal models for spasticity and pain, J. Rehabil Res Dev., Jul.-Aug. 2003, 40(4):41-54, Supplement.
Eggermont, J. J. et al., The neuroscience of tinnitus, Trends Neurosci., Nov. 2004, 27(11):676-682.
Ehrenberger, K., Clinical experience with caroverine in inner ear diseases, Adv Otorhinolaryngol., 2002, 59:156-162.
Fukushima, K. et al., Inhibitory effects of MK801 on activation of MAP kinase in adult rat hippocamus after intracerebroventricular injections of glutamate, somatostatin and neuropeptide Y, Japanese Journal of Pharmacology, Bd. 79, Nr. Suppl. 1, 1998, p. 65P, Abstract O-90.
Gabellini, N., Transcriptional regulation by cAMP and Ca2+ links the Na+/Ca2+ exchanger 3 to memory and sensory pathways, Mol Neurobiol., Aug. 2004, 30(1):91-116 (Abstract).
Ghorbel, M. T. et al, Profile of changes in gene expression in cultured hippocampal neurons evoked by the GABAs receptor agonist baclofen, Physiol Genomics, 2005, 22:93-98.
Goycoolea, M.V. et al., Round window membrane. Structure function and permeability: a review, Microsc Res Tech., Feb. 1997, 36(3):201-211.
Guitton, M. J. et al., Cochlear NMDA Receptors and Tinnitus, Audiological Medicine, 2004, 2(1):3-7.
Guitton, M. J. et al., m-Chlorophenylpiperazine exacerbates perception of salicylate-induced tinnitus in rats, Eur J Neurosci., Nov. 2005, 22(10):2675-2678.
Guitton, M. J. et al., New pharmacological strategies to restore hearing and treat tinnitus, Acta Otolaryngol., May 2004, 124(4):411-415.
Guitton, M. J. et al., Salicylate induces tinnitus through activation of cochlear NMDA receptors, J Neurosci., May 2003, 23(9):3944-3952.
He, X. P. et al., Conditional deletion of TrkB but not BDNF prevents epileptogenesis in the kindling model, Neuron, Jul. 2004, 43(1):31-42.
Hoffer, M. E. et al., Sustained-release devices in inner ear medical therapy, Otolaryngol Clin North Am., Oct. 2004, 37(5):1053-1060.
Kaetsu, I. et al., Controlled release of morphine using polyethylene glycol carrier, Drug Delivery System, 1996, 11(6):399-403 (with English Abstract).
Ito, J. et al., A new method for drug application to the inner ear, ORL J Otorhinolaryngol Relat Spec., 2005, 67(5):272-275.
Jacobson, Tinnitus Handbook, 2000, pp. 194-195.
Jiang, X. et al., CRE-binding protein and NFkappaBare required for N-methyl-D aspartatemediated BDNF promoter III activity in rat hippocampal neurons, Abstracts of the Annual Meeting of the Society for Neuroscience, Society for Neuroscience, Washington, DC, US, Bd. 33,2003 (XP009133108).
Kaltenbach, J. A. et al., Plasticity of spontaneous neural activity in the dorsal cochlear nucleus after intense sound exposure, Hearing Research, Sep. 2000, 147(1-2):282-292.
Kenmochi, M. et al., Salicylate and quinine affect the central nervous system, Hear Res., Nov. 1997, 113(1-2):110-116.
Knipper, M. et al., Thyroid hormone deficiency before the onset of hearing causes irreversible damage to peripheral and central auditory systems, J Neurophysiol., May 2000, 83(5):3101-3112.
Kumagai, M., Effect of intravenous injection of aspirin on the cochlea, Hokkaido Igaku Zasshi, Mar. 1992, 67(2):216-233 (with English Abstract).
Lang, U. E. et al., Association of BDNF serum concentrations with central serotonergic activity: evidence from auditory signal processing, Neuropsychopharmacology, Jun. 2005, 30(6):1148-1153.
Lehner, R. et al., A totally implantable drug delivery system for local therapy of the middle and inner ear, Ear, Nose & Throat Journal, Aug. 1997, 76(8):567-570.

(56) References Cited

OTHER PUBLICATIONS

Lenarz, T. et al., Neural mechanisms of tinnitus, Eur Arch Otorhinolaryngol., 1993, 249(8):441-446.
Light, J. P. et al., Transtympanic perfusion: indications and limitations, Curr Opin Otolaryngol Head Neck Surg., Oct. 2004, 12(5):378-383.
Maier, C. et al., Efficacy of the NMDA-receptor antagonist memantine in patients with chronic phantom limb pain-results of a randomized double-blinded, placebo-controlled trial, Pain, Jun. 2003, 103(3):277-283.
Malawer, M. M. et al., Postoperative infusional continuous regional analgesia. A technique for relief of postoperative pain following major extremity surgery, Clin Orthop Relat Res., May 1991, (266):227-237.
Menkes, D. B. et al., Sodium valproate for tinnitus, J Neural Neurosurg Psychiatry., Nov. 1998, 65(5):803.
Middleton, C., The causes and treatments of phantom limb pain, Nurs Times., Sep. 2-8, 2003, 99(35):30-33 (Abstract).
Obrietan, K., et al, Excitatory Action of GABA increase BDNF Expression via a Mapk-CREB-Dependent Mechanism—A Positive Feedback Circuit in Developing Neurons, J Neurophysiol., 2002, 88:1005-1015.
Oestreicher, E. et al., New approaches for inner ear therapy with glutamate antagonists, Acta Otolaryngol (Stockh), 1999, 119:174-178.
Park, H. et al., Biodegradable Hydrogels for Drug Delivery, CRC Press, 1$^{st}$ Edition, 1993, 2 pages.
Puel, J. L. et al., Treatment of tinnitus. New perspectives, Presse Medical, Jul. 2002, 31(24):1137-1143 (with English Abstract).
Reyes, S. A. et al., Brain imaging of the effects of lidocaine on tinnitus, Hearing Research, Sep. 2002, 171(1-2):43-50.
Sahley, T. L. et al., A biochemical model of preipheral tinnitus, Hearing Research, 2001, 152:43-54.
Sakata, E. et al., Treatment of cochlear-tinnitus with dexamethasone infusion into the tympanic cavity, International Tinnitus Journal, 1996, 2:129-135.
Satterfield, K., Lidocaine relieves tinnitus sufferers, Newswise, American Otological Society (AOS), May 13, 2002, 2 pages.
Savastano, M., Lidocaine intradermal injection—a new approach in tinnitus therapy: preliminary report, Advances in Therapy, Jan.-Feb. 2004, 21(1):13-20.
Schimmang, T. et al., Lack of Bdnf and TrkB signalling in the postnatal cochlea leads to a spatial reshaping of innervation along the tonotopic axis and hearing loss, Development, Oct. 2003, 130(19):4741-4750.
Schwab, B. et al., Use of the round window micro cath for inner ear therapy—results of a Placebo-controlled, prospective study on chronic tinnitus, Laryngorhinootologie, Mar. 2004, 83(3):164-172 (with English Abstract).
Searchfield, G. D. et al., Ensemble spontaneous activity in the guinea-pig cochlear nerve, Hearning Research, Jun. 2004, 192(1-2):23-35.
Selivanova, O. et al., The effects of Streptolysin-O and sodium hyaluronate on the permeability of the round window membrane in guinea pigs—an electrophysiologic study, Laryngorhinootologie, Apr. 2003, 82(4):235-239 (with English Abstract).
Sifringer, M. et al., Neurotrophin-downregulation in the developing brain following treatment with NMDA-antagonists, Abstracts of the Annual Meeting of the Society for Neuroscience, Society for Neuroscience, Washington, DC, US, Bd. 27, Nr. 2, 2001 (XP009133107).
Simpson, J. J. et al., Recent advances in the pharmacological treatment of tinnitus, Trends Pharmacol Sci., Jan. 1999, 20(1):12-18.
Stypulkowski, P. H., Mechanisms of salicylate ototoxicity, Hearing Research, Jun. 1990, 46(1-2):113-145.
Szczepaniak, W. S. et al., Effects of L-baclofen and D-baclofen on the auditory system: a study of click-evoked potentials from the inferior colliculus in the rat, Ann Otol Rhinol Laryngol., May 1995, 104(5):399-404.
Tabata, Y. et al., Biodegradation of hydrogel carrier incorporating fibroblast growth factor, Tissue Engineering, Apr. 1999, 5(2):127-138.
Theopold, H. M., Nimodipine (Bay e 9736) a new therapy concept in diseases of the inner ear?, Laryngol Rhinol Otol (Stuttg)., Dec. 1985, 64(12):609-613 (with English Abstract).
Timmusk, T. et al., Identification of brain-derived neurotrophic factor promoter regions mediating tissue-specific, axotomy-, and neuronal activity-induced expression in transgenic mice, J Cell Biol., Jan. 1995, 128(1-2):185-199.
Vichitrananda, C. et al., Midazolam for the treatment of phantom limb pain exacerbation: preliminary reports, J Med Assoc Thai., Feb. 2001, 84(2):299-302.
Waddell, A. et al., Tinnitus, American Family Physician., Feb. 2004, 69(3):591-592.
Wang, H. et al., Evaluating effects of some medicine on tinnitus with animal behavioral model in rats, Zhonghua Er Bi Yan Hou Ke Za Zhi., Oct. 2000, 35(5):331-334 (Abstract).
Weber, W. E., Pharmacotherapy for neuropathic pain caused by injury to the afferent nerve fibers, Ned Tijdschr Geneeskd., Apr. 2001, 145(17):813-817 (Review).
West, A. E. et al., Calcium regulation of neuronal gene expression, PNAS USA, Sep. 2001, 98(20):11024-11031.
Wiechers, B. et al., A changing pattern of brain-derived neurotrophic factor expression correlates with the rearrangement of fibers during cochlear development of rats and mice, J Neurosci., Apr. 1999, 19(8):3033-3042.
Willingham, E., Tinnitus, Grand Rounds Archieve, Baylor College of Medivine in Houston Texas, Jul. 22, 2004, 8 pages.
Yamada, K. et al., Brain-derived neurotrophic factor/TrkB signaling in memory processes, J Pharmacol Sci., Apr. 2003, 91(4):267-270.
International Search Report and Written Opinion for International Application No. PCT/EP2011/072480, dated May 3, 2012, 18 pages.
Gagnon, Kenneth B. E. et al., Characterization of SPAK and OSR1, Regulatory Kinases of the Na—K—2Cl Cotransporter, Molecular and Cellular Biology, Jan. 2006, vol. 26, No. 2, pp. 689-698.
Wenz, Meike et al., CIP1 is an activator of the $K^+$—$Cl^-$ cotransporter KCC2, Biochemical and Biophysical Research Communications 381, Apr. 10, 2009, (3):388-392, doi: 10.1016/j.bbrc.2009.02.057. Epub Feb. 20, 2009.

* cited by examiner

A) In situ hybridization of spiral ganglion neurons at the cochlear midbasal turn

B) Western Blot of KCC2

A) In situ hybridization of spiral ganglion neurons at the cochlear midbasal turn

*Scale of bar: 50 μm*

B) Count of inner hair cell ribbon synapses

A) KCC2 real time PCR of cochlear tissue

B) Count of inner hair cell ribbon synapses

TREATMENT OF TINNITUS THROUGH MODULATION OF CHLORIDE CO-TRANSPORTER NKCC1 IN THE AUDITORY SYSTEM

CROSS-REFERENCE TO RELATED APPLICATIONS

This application is a Continuation of U.S. patent application Ser. No. 15/166,359, filed on May 27, 2016, now abandoned, which is a Continuation of U.S. patent application Ser. No. 14/364,050, filed on Dec. 12, 2011, now abandoned, which is the National Stage Application of International Patent Application Serial No. PCT/EP2011/072480, filed on Dec. 12, 2011, each of which is herein incorporated by reference in its entirety for all purposes.

The present invention relates to the treatment of tinnitus. More precisely, the present invention relates to a compound modulating chloride co-transporter NKCC1 (chloride co-transporter modulator) for use in tine treatment of tinnitus. In addition, the present invention is directed to pharmaceutical compositions comprising such a chloride co-transporter modulator as an active agent, a method for the treatment of tinnitus by administering such a chloride co-transporter modulator, and a screening method for the identification and characterization of compounds capable of modulating chloride co-transporters.

BACKGROUND OF THE INVENTION

One in ten adults perceives tinnitus, i.e. sound without external acoustic stimulation. For at least 1 in 100 adults tinnitus even seriously impacts the ability to sleep, relax, or to concentrate, or leads to tiredness, irritation, nervousness, despair, frustration, or depression. Since there are, so far, no drugs available with proven efficacy, the treatment of tinnitus still remains a major unmet medical need. Although numerous attempts have been made to elucidate the pathophysiology of tinnitus and to identify pharmacological and other therapies, no attempt provided any more promising curative treatment (Langguth et al., 2009) so far.

To date, it has been proposed that tinnitus is the result of changes in neuronal activity in different parts of the auditory pathway (Langguth et al., 2009). According to this hypothesis, a decrease in inhibition and/or increase in excitation may lead to an excitatory-inhibitory imbalance in the auditory system. This imbalance is suggested to cause neural hyperexcitability in the auditory pathway leading to the perception of phantom sound. In this respect, it has been experimentally shown that cochlear dysfunction, e.g. resulting from noise overexposure or ototoxic drugs, leads to diminished afferent output to central auditory structures, reduced inhibition in these structures, and as a result increased spontaneous firing rates (Eggermont and Roberts, 2004).

In this context, down-regulation of inhibition mediated by gamma-amino butyric acid (GABA), a major inhibitory neurotransmitter of the auditory pathway, has been suggested as a potential mechanism for such loss of inhibition in central auditory structures (Bauer and Brozoski, 2007). Correspondingly, administration of GABAergic pharmacological agents was expected to enhance inhibition in the auditory system, and thus, to attenuate the perception of tinnitus.

For this reason, various GABAergic pharmacological agents have been tested as potential tinnitus curing agents in animal models or clinical trials. More precisely, $GABA_A$, receptor ligands such as benzodiazepines, $GABA_B$ receptor ligands such as baclofen, GABA transaminase inhibitors such as valproate, or GABA analogues such as gabapentin have been tested for their efficacy to treat tinnitus.

However, studies with baclofen (Westerberg et al., 1996) or gabapentin (Piccirillo et al., 2007) showed no effects at all. Empirical evidence with valproate is contradictory, i.e. there are reports of tinnitus relief and of tinnitus induction (Menkes and Larson, 1998). Another GABA transaminase inhibitor, vigabatrin, was tested by Brozoski et al., 2007 in an animal modes of chronic tinnitus induced by noise trauma. The behavioural correlate of tinnitus was reversibly suppressed by the vigabatrin treatment, which was explained by the authors by its affect on the central auditory pathway. Clinical trials with various benzodiazepines were inconclusive (Dobie 2004, Langguth et al., 2009). There has been one study claiming successful tinnitus control by combined administration of clonazepam and gabapentin, however, neither a randomized nor controlled design has been performed (Shulman et al., 2002).

Following similar logic to the GABA-based hypothesis, inhibition mediated by another major inhibitory neurotransmitter Glycine has also been suggested as a target for a tinnitus treatment in this, respect WO 2009/080268 discloses the presence of glycine receptors in the cochlea and teaches local administration of glycine agonists for the treatment of tinnitus. However, no data documenting success of such an approach have been provided. Since, however, glycine is a co-agonist along with glutamate for NMDA receptors, it might also have an opposing excitatory effect.

From the above, it is obvious that the clinical evidence for effective treatment of tinnitus with GABAergic and/or glycinergic pharmacological agents as well as their suggested mechanism of action is rather confusing and may depend on various factors not yet known.

Therefore, in order to provide novel, effective compounds for the treatment of tinnitus, there is a need in the art, to better understand the mechanism underlying the above-mentioned excitatory-inhibitory imbalance in the auditory system.

For the central nervous system, which is far better understood than the auditory system, it is known that strength and polarity of $GABA_A$ receptor- and glycine receptor-mediated synaptic currents can be controlled via modification of the transmembrane concentration gradient of ions to which these receptors are permeable (in particular, chloride and bicarbonate). For instance, the concentration of chloride in neurons of the central nervous system is usually very low. Thus, small changes in chloride concentration are suggested to have a large impact on the transmembrane gradient, which can significantly affect how ion currents through $GABA_A$ or glycine receptor channels modify the membrane potential in the central nervous system (De Koninck, 2007).

In addition, it is known that chloride homeostasis in cells of the central nervous systems is maintained, among other molecular elements, by cation-chloride co-transporters (CCCs) and $Cl^-$—$HCO_3^-$ exchangers (De Koninck, 2007). The CCC family in mammals consists of nine family members encoded by the genes Slc12al-9 (Blaesse et al., 2009). In terms of their function the CCCs fall into three categories: Na—K-2Cl co-transporters (NKCCs; isoforms NKCC1 and NKCC2), Na—Cl co-transporter (NCC), and K—Cl co-transporters (KCCs; isoforms KCC1-4). The two dominant CCCs pertinent to neurons of the central nervous system are: NKCC1 which normally mediates uptake of chloride, whereas KCC2 normally extrudes chloride. (De Koninck, 2007). Ultimately, both co-transporters depend on gradients established by the Na—K-ATPase, using K$^+$ and N$^+$ gradients, respectively, to extrude or import Cl$^-$ ions (Payne et al., 2003).

NKCC1 is widely distributed throughout the body. NKCC1 transports sodium, potassium, and chloride into the cell. NKCC1 is also found throughout the nervous system where it is expressed on astrocyte, oligodendrocytes, and Schwann cells (Lenart et al., 2004). Another isoform, NKCC2 is found primarily in the kidney, where it serves to extract sodium, potassium, and chloride from the urine (Haas, 1994). The regulation of Cl$^-$ transport into and out of cells plays a critical role in the maintenance of intracellular volume and the excitability of GABA responsive neurons regulated by at least two ion cotransporters: Cl$^-$ influx is mediated by NKCC1 which mediates the Cl$^-$ influx and KCC1 or KCC2 which mediate the Cl$^-$ efflux (Kahle et al., 2005). The maintenance of intra- and extracellular electrolyte homeostasis is required for a wide range of essential physiologic processes including general functions (e g maintenance of proper cell volume), specialized cell functions (e.g., control of neuronal excitability), and global functions (e.g., regulators of blood pressure.) This homeostasis is achieved via the regulated movement of Na$^+$, K$^+$, and Cl$^-$ across cell membranes by ion channels, cotransporters, exchangers, and pumps that execute transmembrane electrolyte flux (Kahle et al., 2005). The predominant mechanism by which intracellular volume is maintained in cells in response to changes in extracellular tonicity is the raising or lowering of intracellular Cl$^-$ concentration, thereby minimizing transmembrane water flux. Intracellular Cl$^-$ concentration is modulated by altering the balance between Cl$^-$ entry and exit. The major mediator of Cl$^-$ entry is NKCC1 and Cl$^-$ exit is largely mediated by KCC1-. These cotransporters are both regulated by extracellular tonicity: hypertonicity activates NKCC1 and inhibits KCC1, whereas hypotonicity has the opposite effect (Kahle et al., 2005).

As stated above, the intracellular Cl$^-$ concentration in neurons of the central nervous system is held low under normal conditions, and the Cl$^-$ reversal potential ($E_{Cl}$) in neurons around or below the resting potential. Whenever GABA or glycine gate GABA$_A$ or glycine channels, respectively, this typically causes inhibition either via a hyperpolarising chloride influx, or through shunting inhibition, depending on whether $E_{Cl}$ is more negative, or similar to, the resting potential (Payne et al., 2003). However, should disruption of Cl$^-$ homeostasis cause levels of intracellular Cl$^-$ to rise, $E_{Cl}$ can become less negative than the resting potential. In this instance opening of GABA$_A$ or glycine channels results in little or no inhibition and in extremis, in Cl$^-$ efflux from the cell, with a net depolarizing, excitatory effect.

In this context, it was shown that BDNF-induced trkB activation down-regulates KCC2 expression in hippocampal brain slices, which results in suppression of chloride-dependent fast GABAergic inhibition (Rivera et al., 2002). Similar observations have been made in the dorsal horn of the spinal cord (Couil et al., 2005). More precisely, it has been shown that under pathological conditions, secretion of BDNF leads to down-regulation of KCC2 expression, which decreases the chloride extrusion capacity of cells of the central nervous system. Thus, Cl$^-$ accumulates within the cell and shifts $E_{Cl}$, resulting in a decrease in inhibition of the cells of the central nervous system (Rivera et al., 2002, De Koninck, 2007). It appears that the anion flux is inverted in such a situation, and GABA as well as glycine becomes depolarizing, substantially enhancing the excitability of the cells. In addition, it is also known that up-regulation of NKCC1 acts synergistically with down-regulation of KCC2 (De Koninck, 2007) Recently, it was speculated in a publication by Lee et al. (2011) that KCC2 function may be dependent on the phosphorylation of Ser940, since loss of function (e.g. due to elevated glutamate levels) was observed when dephosphorylation of Ser940 was mediated by protein phosphatase 1. Accordingly, the mechanism underlying KCC2 down-regulation may be based on the phosphorylation status of Ser940.

Recently, it was shown, that under physiological conditions GABA$_A$ receptor channels and also glycine receptors mediate substantial currents, carried not only by Cl$^-$, but also by $HCO_3^-$(Asiedu et al., 2010). Thus, a reduced Cl$^-$ extrusion capacity will favour depolarization of channel-mediated efflux of $HCO_3^-$, especially in neurons of the central nervous system equipped with cytoplasmic carbonic anhydrase. Since this enzyme is able to quickly replenish intracellular $HCO_3^-$ during the channel-mediated net efflux, the $HCO_3^-$-dependent depolarization may become large enough to result in GABAergic or glycinergic excitation during ongoing neuronal network activity. Therefore, it is suggested that inhibition of carbonic hydrase reduces $HCO_3^-$-mediated excitatory GABAergic and/or glycinergic currents.

All the above-mentioned findings hold for neuronal cells of the central nervous systems. However, it is commonly known that neuronal cells of the central nervous systems, developing from neurocrest cells, are different in their evolution, structure and behaviour to neuronal cells developing from placodes such as in the auditory system. For example, hippocampal neurons are multipolar cells having a single axon and multiple dendrites, whereas neurons of the cochlea are bipolar, i.e. possess a single axon and a single dendrite. Moreover, CNS neurons receive a direct inhibitory input from GABA-glycinergic interneurons, while auditory neurons in the periphery receive it indirectly through a synaptic network (superior olivary complex) in the brainstem that feeds back to the afferent peripheral neurons via axodendritic terminals. Thus, the above-mentioned findings for the central nervous system cannot be conferred at all to the auditory system. In the auditory system, the mechanisms are far less well studied.

Therefore, the above-mentioned findings for the central nervous system cannot be presumed to underlie any excitatory-inhibitory imbalance in the auditory system. Indeed, any excitatory-inhibitory imbalance in the cochlear may be due to disruption on either excitatory and/or inhibitory sides of the balance. Moreover they could conceivably be due to myriad mechanisms, including alterations to excitatory and/or inhibitory channel expression channel conductance, synaptic strength and connectivity, or disruption of any of the ion gradients that dictate resting membrane potential, membrane resistance, or the reversal potential of key ions.

For the auditory system, it is merely known that the pro-survival and pro-regenerative neurotrophin BDNF is an otoprotective agent that is required for normal auditory development and survival of adult neurons (Meltser et al., 2010). Beyond that, a significant elevation of BDNF expression in spiral ganglion neurons of rats, exposed to a tinnitus inducing acoustic trauma; has been reported by Tan et al., 2007. This is accompanied by augmented expression of BDNF and GABA in the inferior colliculus. However, that involves a significant reduction of BDNF expression in the auditory cortex.

In contrast, EP 1843757 B1 discloses that the expression of the brain-derived nerve growth factor "BDNF" is increased during acute tinnitus, i.e. tinnitus which occurs for less than three months. In addition, EP 1843757 B1 teaches that administration of GABA receptor agonists results in significantly reduced BDNF expression in the cochlear neurons and reduced symptoms of acute tinnitus. Since, however, the effect of BDNF (i.e. on the BDNF signal transduction cascade) is mediated via specific receptors, such as the BDNF receptor trkB, it has been suggested that GABA receptor agonists interact with the BDNF signal transduction cascade upstream of trkB.

Beyond that, expression of KCC2, KCC3 and KCC4 has been identified in the cochlea (Yang et al., 2008), in the cochlear nucleus (Vale et al., 2005), and in the lateral superior olive (Balakrishnan et al., 2003). In animal studies, the disruption of cochlear KCC3 and KCC4 caused deafness. In this context it has been hypothesized that such a degeneration is, among other factors, the result of disturbed cochlear potassium recycling, which is essential for maintaining the endocochlear potential. It has been also suggested that KCC2 may be a switch controlling the depolarization or hyperpolarization of spiral ganglion neurons and may play an important role in the functioning of GABA (Yang et al., 2008). NKCC1 has been localized in animal cochleae as well and it has been shown that this co-transporter plays a critical role in the transepithelial $K^+$ transport and maintenance of the endocochlear potential; mice lacking NKCC1 were found profoundly deaf (Flagella et al., 1999).

Carbonic anhydrases have also been localized in cochlear hair cells as well as in spiral ganglion cells (Okamura et al., 1996) and have been reported to occur at least in developing rat auditory brainstem neurons (Backus et al., 1998). In this context, WO 2007/012064 by Anderson et al. describe the use of the carbonic anhydrase inhibitor and diuretic zonisamide either alone or in combination with other compounds for the treatment of hearing disorders, including tinnitus. Administration of zonisamide is taught as a treatment since it complements the pharmacology of a norepinephrine-epinephrine re-uptake inhibitor by: 1) enhancing serotonin and dopamine transmission and 2) by blocking sodium and calcium channels.

WO 03/10007S teaches the use of substances altering the function of ClC—K/barttin channels to treat diseases of the inner ear, including tinnitus. ClC—K/barttin channels are voltage gated and have been reported to play an important role in potassium secretion from strial marginal cells into endolymph, thus contributing to the maintenance of the endolymphatic potential (Lang et al., 2008). However, the mechanism, by which the disclosed substances are expected to have an effect on tinnitus, is not disclosed therein.

In addition, the use of loop diuretics or carbonic anhydrase inhibitors for the treatment of endolymphatic hydrops or Meniere's Disease, respectively, is known. Both reduce cell volume and are supposed to relieve ear fluid pressure. For instance, US 2003/229333 describes a sustained release drug delivery device for delivering medicaments to the inner ear, such as diuretic agents, including but not limited to thiazide, triamterene and carbonic anhydrase inhibitors.

The aim is to decrease inner ear fluid volume by diuresis. Since diuretics reduce the endocochlear potential, it has been hypothesized that they also attenuate the firing of the auditory nerve and could thus treat also tinnitus (Risey et al., 1995). The loop diuretic furosermide has indeed been shown to suppress tinnitus, albeit only in a reversible fashion and not in all patients; and effects were reported only for tinnitus of cochlear, rather than central origin (Risey et al., 1995). Yet at the same time, furosemide administered at high doses is known to induce temporary tinnitus and hearing loss, occasionally also irreversibly. Since furosemide influences or rather inhibits numerous enzyme or transporter systems—$K^+$—$Cl^-$ exchange, $Na^+$—$K^+$—$Cl^-$ co-transport, carbonic anhydrase, $Cl^-/HCO_3^-$ exchange, and even some $GABA_A$ receptors—it is difficult to identify its locus of action (Saley, 2002) and its specific effect on tinnitus. Furosemide's principal effect will be inhibition of $Cl^-$ export if cells are loaded with chloride, but if neurons are $Cl^-$ depleted, the principal effect will be inhibition $Cl^-$ uptake (idern). Tinnitus and hearing dysfunction have also been reported as side effects of the carbonic anhydrase inhibitor acetazolamide.

WO 2010/085352 discloses the use of bumetanide, furosemide, piretanide, azosemide and torsemide analogs for the treatment of diseases, disorders, and conditions that involve the $GABA_A$ receptor, including tinnitus. Referring to Brozoski et al., 2007, and the known fact that disruption of NKCC1 results in deafness, the inventors conclude that therapeutics targeting GABAergic system and/or NKCC1 may be useful in the treatment of tinnitus. Disclosed are compounds that antagonize NKCC1 and/or $GABA_A$. In particular. WO 2010/085352 discloses antagonists specific for α4 $GABA_A$ variants which lead to an increased GABA release and subsequent increase in the inhibitory signalling to restore the balance between excitation and inhibition in the central nervous system. In preferred embodiments, compounds such as bumetanide that have as such a diuretic effect, are rendered non-diuretic through methods of medicinal chemistry in order to prevent them to act on NKCC1. With regards to NKCC1, the inventors of WO 2010/035352 are thus disclosing contradicting approaches. By reference, to Brozoski et al., 2007, the inventors of WO 2010/085352 seek to treat chronic tinnitus in the central auditory pathway, but not acute or sub-acute tinnitus, and not in the cochlea. No experimental data are provided to show efficacy of their compounds in the treatment of tinnitus.

In summary, it becomes obvious from the above-mentioned summary of the art that the mechanisms in the auditory system in general and the mechanisms leading to tinnitus in particular, are extremely complex and involve a multitude of unanswered questions and observations, which are not well understood.

Thus, it would provide a major break-through, if there were a better understanding of the precise mechanism underlying the above-mentioned excitatory-inhibitory imbalance of the auditory system. That would lead to urgently needed novel and effective compounds for the treatment of tinnitus.

Therefore, it was an object of the present invention to provide novel compounds suitable to interfere with the excitatory-inhibitory imbalance and, thus, suitable to be used for specific and targeted treatment of tinnitus. Further, it was an object of the present invention to provide novel pharmaceutical compositions and novel methods for the treatment of tinnitus.

The object of the present invention, in one preferred embodiment thereof, is solved by a compound modulating the chloride co-transporter NKCC1 for use In the treatment of tinnitus. In particular, the object is solved by modulation of NKCC1 through NKCC1 antagonists. More particularly, the object is solved by NKCC1 antagonists, whereby such NKCC1 antagonism results in an up-regulation of the activity and/or expression of KCC2.

In a further preferred embodiment, the object of the present invention is solved by a pharmaceutical composition comprising, as an active agent, a compound modulating chloride co-transporter NKCC1 according to the present invention.

Additionally, the object of the present invention, in a preferred embodiment thereof, is solved by a method for the treatment of tinnitus,, comprising administering a therapeutically effective amount of a compound modulating chloride co-transporter NKCC1 or a pharmaceutical composition according to the present invention.

In a further embodiment, the present invention is related to a screening method for the identification and characterization of compounds capable of modulating chloride transporter NKCC1.

As a result of the experiments carried out for the present invention, it was found, that a compound modulating chloride co-transporter NKCC1 is suitable for the treatment of prevention of tinnitus.

In particular, it was found that there is a correlation between disturbances of chloride homeostasis in the auditory system and the perception of tinnitus. More precisely, it was experimentally proven that a pathologically altered expression/activity of KCC2 correlates with aberrant auditory neurotransmission perceived as tinnitus.

In this respect, the inventors of the present invention found that injury to the auditory system e.g. from acoustic trauma leads to a significant down-regulation of chloride co-transporter KCC2 In the auditory system, such as in inner hair cells and spiral ganglion neurons (Example 1), which is specific for the presence of tinnitus (Example 2).

Beyond that, it was demonstrated, that the use of compounds which modulate intracellular chloride levels by modulating chloride co-transporter NKCC1 are effective in the suppression of tinnitus (Example 3) and increase activity and/or expression of KCC2.

Thus, it was experimentally proven that tinnitus results from disturbance of chloride homeostasis by disturbance of the expression of chloride co-transporter KCC2 in sensorineural structures of the auditory system. From that, it is concluded that down-regulation of KCC2 does not lead to hearing loss, but rather to tinnitus. Additionally, it was shown that NKCC1 antagonism does interfere with that pathophysiological mechanism. Accordingly, compounds acting as NKCC1 antagonists may therefore be used for the treatment or prevention of acute or chronic tinnitus. NKCC1 antagonism may decrease the expression and/or activity of chloride co-transporter NKCC1, preferably in sensorineural structures of the auditory system, more preferably, in cochlear hair cells, spiral ganglion neurons or other neural cells along the auditory pathway, the antagonism may e.g. be due to down-regulation of the NKCC1 expression (on ether the transcription and/or the translation level) or e.g. by blocking the NKCC1 chloride up-taking activity in a competitive or non-competitive manner. NKCC1 antagonistic compounds of the invention are capable of modulating, preferably decreasing, intracellular chloride levels in a sensorineural cell of the auditory system. As shown below, compounds that modulate activity/expression of NKCC1 can be used for decreasing intracellular chloride levels and ultimately prevent or treat tinnitus.

By the inventive compounds, the excitatory-inhibitory balance of the auditory system is reconstituted, which diminishes the phantom sound phenomena of tinnitus. Down-regulation of the co-transporter KCC2 accompanied by accumulation of intracellular chloride anions. Without being bound to any theory, this may cause a collapse in the transmembrane chloride gradient and a decrease in hyperpolarizing inhibition of the cells; indeed, in most cases, the anion flux is inverted, and GABA (as well as glycine) becomes depolarizing, substantially enhancing the excitability of the cells (de Koninck, 2007). This results then in excitatory-inhibitory imbalance. Since down-regulation of KCC2 acts synergistically with up-regulation of NKCC1, NKCC1 is also involved in the excitatory-inhibitory imbalance resulting in tinnitus. Therefore, a compound modulating NKCC1 chloride transport by an antagonistic mode results in an up-regulation of KCC2 expression and/or activity and may be used for the treatment or prevention of acute or chronic tinnitus according to the present invention. Preferably, the compound modulates the NKCC1 co-transporters in sensorineural structures of the auditory system, more preferably, in cochlear hair cells, spiral ganglion neurons or other neural cells along the auditory pathway.

"Up-regulation" or "increase" of KCC2 activity and/or expression as used herein, refers broadly to a quantified change in a measurable quality that is larger than the margin of error inherent in the measurement technique, preferably an increase to at least 60% of the non-pathologic level, more preferably an increase to at least 80%, and most preferably an increase to 90% or even 100% of such level, i.e. full restoration of KCC2 activity and/or expression. In particular, the term "up-regulation or increase," of KCC2 activity and/or expression as used herein, refers broadly to enhance KCC2 expression either by enhancing its transcription and/or its translation, thereby increasing the KCC2 activity measured for a cell.

Alternatively, it refers to the activity of the KCC2 protein, namely its activity to maintain the cell's Cl- homeostasis by enhancing its co-transporter activity, e.g. by avoiding its dephosphorylation at Ser940.

The term "sensorineural structures of the auditory system" in the context of the present invention refers to the auditory pathway, comprising cochlea, spiral ganglion neurons, auditory nerve, trapezoid body, cochlear nuclei, superior olivary nucleus, lateral lemniscus, inferior colliculus, thalamus, and the auditory cortex. It also comprises somatosensory neurons and pathways projecting to the auditory pathway, since pathologies, such as cranio-cervical imbalances, or disorders of the temporomandibular joint, jaws or extra-ocular muscles, may evoke tinnitus as a symptom as well. The term "up-regulation" is meant to include an up-regulation in activity which may be e.g. due to an up-regulation of the expression level or other phenomena leading to an up-regulation or increase in activity.

Therefore, in a first aspect the present invention relates to a compound modulating chloride co-transporters NKCC1 for the use in the treatment or prevention of acute or chronic tinnitus. Preferably, such a compound modulates chloride co-transporter NKCC1 in sensorineural structures of the auditory system, and, more preferably, in cochlear hair cells, spiral ganglion neurons or other neural cells along the auditory pathway. More specifically, inventive NKCC1 antagonistic compounds counteract additionally the down-regulation of the chloride co-transporter KCC2 in inner hair cells and spiral ganglion neurons, thereby reversing partially or completely the pathophysiological down-regulation of KCC2 (leading to tinnitus) which results from injury to the auditory system.

More specifically, the compound modulating co-transporter NKCC1 decreases the intracellular chloride level, preferably in sensorineural structures of the auditory system, more preferably, in cochlear hair cells, spiral ganglion neurons or other neural cells along the auditory pathway. The compound modulating chloride co-transporter NKCC1 may preferably decrease the intracellular chloride level, thereby increasing activity and/or expression of KCC2, preferably, in sensorineural structures of the auditory system, more preferably, in cochlear hair cells, spiral ganglion neurons or other neural cells along the auditory pathway. Hereby, the compound modulating chloride co-transporter NKCC1 may specifically increase expression or activity of the chloride co-transporter KCC2, preferably in sensorineural structures of the auditory system, more preferably, in cochlear hair cells, spiral ganglion neurons or other neural cells along the auditory pathway.

Preferably, the compound decreasing the expression and/or activity of the chloride co-transporter NKCC1 does not bind to KCC2 at all. Even though the NKCC1 antagonistic compound may have—in some instances—a (minor) antagonistic effect on KCC2, it is more preferably to use compounds that either have no direct interaction with KCC2 (i.e. which do not bind to KCC2 at all) or, even more preferably, may also directly interact with KCC2 in an agonistic way increasing the expression and/or activity of KCC2. Accordingly, the NKCC1 antagonistic compound of the invention should preferably have an agonistic (i.e. reciprocal) effect on KCC2.

Preferably, the NKCC1 antagonistic compound decreasing the expression and/or activity of chloride co-transporter NKCC1 being used for the treatment and/or prevention of tinnitus is selected from the group comprising sulfonamides, e.g. acetazolamide, azosemide, bumetanide, chlorthalidone, clopamide, furosemide, hydrochlorothiazide (HCT, HCTZ, HZT), indapamide, mefruside, metolazone, piretanide, tripamide xipamide, dichlorphenamide (DCP), dorzolamide, ethoxzolamide, sultiame, or zonisamide or analogs thereof. Alternatively, the compound decreasing the expression and/or activity of the chloride co-transporter NKCC1 is selected from the group comprising the class of thiazide and thiazide-like diuretics, e.g. bendroflumethiazide, benzthiazide, chlorothiazide, hydrochlorothiazide, hydroflumethiazide, methylclothiazide, polythiazide, trichlor-methiazide, chlorthalidone, indapamide, metolazone or quinethazone or analogs thereof. Alternatively, the compound decreasing the expression and/or activity of the chloride co-transporter NKCC1 is selected from the group comprising sulfonyl urea such as torsemide, or phenoxyacetic acid derivative such as ethacrynic acid, or muzolimine.

"Analogs," as used herein, refer broadly to the modification or substitution of one or room chemical moieties on a parent compound and may include derivatives,, positional isomers, and prodrugs of the parent compound. Loop diuretics, like bumetanide, furosemide, pinetanide, azosemide, and torsemide or analogs thereof, are preferred. Their nomenclature is derived from their potent diuretic effect. Loop diuretics antagonists of the $Na^+K^+Cl^-$ cotransporter (e.g. NKCC1) in the thick ascending limb of the loop of Henle and act to inhibit sodium and chloride reabsorption by competing for the $Cl^-$ binding site (see also Russell, 2000). Diuretics, in particular loop diuretics, may simultaneously act as carbonic anhydrase inhibitors reducing intracellular chloride levels. Insofar, diuretics selected from the group consisting of acetazomalide, dichlorphenamide, dorzolamide, brinzolamide and methazolamide are preferred as carbonic anhydrase inhibitors.

Preferred according to the present invention is the use of bumetanide or analogs thereof having NKCC1 antagonistic effects for the treatment and/or prevention of -tinnitus.

Particularly preferred are compounds according to the following formula I

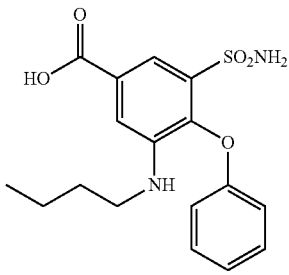

whereby R1, R2, R3 and R4 are each independently hydrogen, alkyl, cycloalkenyl, alkenyl, cycloalkenyl, alkoxy, carboxy, alkylhalo, aryl, aryloxy, alkaryloxy, alkaryl, alkylamino(di)alkyl, alkylheterocycloalkyl and whereby R5 and R6 are each independently hydrogen, hydroxyl, carboxy, amino, substituted amino, alkyl, alkylene, halo.

At R1, R2, R3, and/or R4 a biocompatible polymer may be chosen as substituent as well. Such a biocompatible polymer may alternatively also be covalently linked (via a linker moiety or without a linker moiety) to formula I at any other appropriate group of a compound according to formula I.

"Alkenyl" as used herein, refers broadly to a straight or branched chain hydrocarbon radical having one or more double bonds and containing from 2 to 20 carbon atoms. Examples of alkenyl groups include propenyl, butenyl, pentenyl, and the like. "Cycloalkenyl" or "cyclic alkenyl" as used herein refers to carbocycles containing no heteroatoms, and includes mono-, bi-, and tricyclic saturated carbocycles, as well as fused rings systems. Examples of cycloalkenyl groups include cyclopropenyl, cyclopentenyl, cyclohexenyl, cyclopentadienyl, cyclohexadienyl, and the like. Such alkenyl and cycloalkenyl groups may be optionally substituted as described herein.

"Alkyl" as used herein refer broadly to a straight or branched chain saturated hydrocarbon radical. "Alkyl" also refers broadly to cyclic (i.e., cycloalkyl) alkyl groups. Examples of alkyl groups include, but are not limited to, straight chained alkyl groups including methyl, ethyl, n-propyl, n-butyl, n-pentyl, n-hexyl, n-heptyl, n-octyl, and branched alkyl groups including isopropyl, test-butyl, isoamyl, neopentyl, iso-amyl, and the like. "Cycloalkyl" or "cyclic alkyl" as used herein refers to carbocycles containing no heteroatoms, and includes mono-, bi- and tricyclic saturated carbocyles, as well as fused ring systems. Examples of cycloalkyl include cyclopropyl, cyclobutyl, cyclopentyl, cyclohexyl, cycloheptyl, and the like. The cycloalkyl can be substituted or unsubstituted, and cyclic alkyl groups including cyclopropyl, cyclopentyl, cyclohexyl, cycloheptyl, and the like. Such alkyl groups may be optionally substituted as described herein.

"Alkylhalo" refers broadly to a straight or branched chain, saturated or partially unsaturated hydrocarbon radical bonded to a halogen (e.g., fluoro, chloro, bromo, and iodo).

"Alkaryl" as used herein refers broadly to a straight or branched chain, saturated hydrocarbon radical bonded to an aryl group. Examples of alkaryl groups include, but are not limited to, benzyl, 4-chlorobenzyl, methylbenzyl, dimethyl-benzyl, ethylphenyl, propyl-(4-nitrophenyl), and the like. Such alkaryl groups may be optionally substituted described herein.

"Aryl" or "Ar" as used herein refers broadly to an aromatic group or to an optionally substituted aromatic group fused to one or more optionally substituted aromatic groups, optionally substituted with suitable substituents including, but not limited to, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl 2-naphthyl, 1-naphthyl, and the like.

"Alkoxy" as used herein alone or as part of another group, refers broadly to an alkyl group, as defined herein, appended to the parent molecular moiety through an oxy group. In some embodiments, the alkyl group can be interrupted by one or more heteroatoms (e.g., O, S, or N). Examples of alkoxy include, but are not limited to, methoxy, ethoxy, propoxy, 2-propoxy, butoxy, tert-butoxy, pentyloxy, hexyloxy, ethyloxyethyl, and the like.

"Alkaryloxy" or "oxyalkaryl" as used herein refers broadly to the group —O-alkyl-aryl wherein Ar is aryl. Examples include, but are not limited to, benzyloxy, oxybenzyl, 2-naphthyloxy, and oxy-2-naphthyl.

"Alkaryloxyalkyl" or "alkyloxyalkaryl" as used herein refers broadly to the group -alkyl—O-alkyl-aryl wherein Ar is aryl. Examples include, but are not limited to benzyloxyethyl.

"Aryloxy" as used herein refers broadly to the group —ArO wherein Ar is aryl or heteroaryl. Examples include, but are not limited to, phenoxy, benzyloxy, and 2-naphthyloxy.

"Biocompatible polymer" as used herein refers broadly to a polymer moiety that is substantially non-toxic and does not tend to produce substantial immune responses, clotting or other undesirable effects. Accordingly to some embodiments of the present invention, polyalkylene glycol is a biocompatible polymer where, as used herein, polyalkylene glycol refers to straight or branched polyalkylene glycol, such as polyethylene, polypropylene and polybutylene glycol, and further includes the monoalkylether of the polyalkylene glycol. In some embodiments of the present invention, the polyalkylene glycol polymer is a lower alkyl polyalkylene glycol moiety such as a polyethylene glycol moiety (PEG), a polypropylene glycol moiety, or a polybutylene glycol moiety. PEG has the formula —HO(CH2CH2O)nH, where n can range from about 1 to about 4000 or more. In some embodiments, n is 1 to 100, and in other embodiments, n is 5 to 30. The PEG moiety can he linear or branched. In further embodiments, PEG can be attached to groups such as hydroxyl, alkyl, aryl, acyl, or ester. In some embodiments, PEG can be an alkoxy PEG, such as methoxy-PEG (or mPEG), where one terminus is a relatively inert alkoxy group, while the other terminus is a hydroxyl group.

"Carboxy" as used herein refers broadly to the group —COOH.

"Cycloalkyl" as used herein refers to carbocycles containing no heteroatoms, and includes mono-, bi- and tricyclic saturated carbocycles, as well as fused ring systems. Examples of cycloalkyl include cyclopropyl, cyclobutyl, cyclopentyl, cyclohexyl, and the like. The cycloalkyl can be substituted or unsubstituted.

"Halo" as used herein refers broadly to bromo, chloro, fluoro, or iodo. Alternatively, the term "halide" as used herein refers broadly to bromide, chloride, fluoride, or iodide.

"Hydroxy" as used herein refers broadly to the group —OH.

"Heteroaryl" as used herein refers to an aromatic five- or six-membered ring where at least one atom consists of a heteroatom (e.g., O, S, or N), and the remaining atoms are carbon. The five-membered rings have two double bounds, and the six-membered rings have three double bonds. The heteroaryl group can be monocyclic or bicyclic (fused or non-fused). Examples of monocyclic heteroaryl groups include furanyl, thiophene-yl, pyrrolyl, oxazolyl, thiazolyl, imidazolyl pyrazolyl, isoxazolyl, isothiazolyl, oxadiazolyl, thiazolyl, thiadiazolyl, pyridinyl, pyridazinyl, pyrimidinyl, pyrazinyl, triazinyl, and the like. Examples of bicyclic heteroaryl groups include indolizinyl, indolyl, isoindolyl, benzofuranyl, benzothiophene-yl, indazolyl, benzimidazolyl, benzthiazolyl, purinyl, quinolinyl, isoquinolinyl, cinnolinyl, phthalazinyl, quinazolinyl, quinoxalinyl, napthyridinyl, pteridinyl, and the like. The heteroaryl group can be substituted or unsubstituted.

"Heterocycloalkyl" as used herein refers to a cycloalkyl group where at least one of the carbon atoms in the ring is replaced by a heteroatom (e.g., O, S, or N). The heterocycloalkyl group can be monocyclic or bicyclic (fused or non-fused). Examples of monocyclic heterocycloalkyl groups include azetidinyl, pyrrolidinyl, piperidinyl, homopiperidinyl, piperazinyl, morpholinyl, thiomorpholinyl, 1-oxothiomorpholinyl, 1,1-dioxothiomorpholinyl, tetrahydrooxazolyl, tetrahydroisoxazolyl, tetrahydroimidazolyl, tetrahydropyrazolyl, tetrahydrothiazolidinyl, tetrahydroisothiazolidinyl, tetrahydropyrimidinyl, tetrahydropyridazinyl, 4-piperadonyl, and the like. Examples of bicyciic non-fused heterocycloalkyl groups include quinuclidinyl, adamantyl, 2-azobicyclo[3,2,1]octyl, and the like. Examples of fused heterocycloalkyl groups include any of the aforementioned monocyclic heterocycloalkyl groups fused with another cycloalkyl or heterocycloalkyl group. The heterocycloalkyl group can be substituted or unsubstituted.

"Substituted" as used above refers broadly to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, arylalkaryl, hydroxyl, thioalkoxy, aryloxy, acyl, amino, amido, carboxy, carboxyalkyl, thiocarboxyalkyl, carboxyaryl, thiocarboxyaryl, halo, oxo, mercapto, sulfinyl, sulfonyl, sulfonamido, amidino, carbamoyl, cycloalkyl, heterocycloalkyl, dialkylaminoalkyl, carboxylic acid, carboxamido, haloalkyl, dihaloalkyl, trihaloalkyl, trihaloalkoxy, alkylthio, aralkyl, alkylsulfonyl, arylthio, amino, alkylamino, dialkylamino, guanidino, ureido, nitro and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent or reagent.

NKCC1 antagonistic compounds as disclosed herein, e.g. according to formula I are e.g. provided as isomers, tautomers, zwitterions, enantiomers, diastereomers, racemates, or stereochemical mixtures thereof. They will typically be provided as e.g. a pharmaceutically acceptable salt, solvate, hydrate, or combination thereof and are typically formulated as a pharmaceutical composition in combination with a pharmaceutically acceptable carrier, excipient, or diluent.

"Pharmaceutically acceptable salt" as used herein, refers broadly to a salt form of a compound permitting its use or formulation as a pharmaceutical and which retains the biological effectiveness of the free acid and base of the specified compound and that is not biologically or otherwise undesirable. Pharmaceutically acceptable salts of the compounds described herein include the salt form of the compound permitting its use or formulation as a pharmaceutical and which retains the biological effectiveness of free acid and base of the speeded compound and that is not biologically or otherwise undesirable. Examples of such salts are described in Wermuth and Stahl, (Eds.) (2002) Handbook of Pharmaceutical Salts: Properties, Selection, and Use, Wiley-Verlag Helvetica Acta, Zurich, herein incorporated by references in its entirety. Examples of such salts include alkali metal salts and addition salts of free acids and bases. Examples of pharmaceutically acceptable salts, without limitation, include sulfates, pyrosulfates, bisulfates, sulfites, bisulfites, phosphates, monohydrogenphosphates, dihydrogen phosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, gamma-hydroxybutyrates, glycolates, tartrates, methanesulfonates, ethane sulfonates, propanesulfonates, toluenesulfonates, naphthalene-1-sulfonates, naphthalene-2-sulfonates and mandelates. In some embodiments, pharmaceutically acceptable salt includes sodium, potassium, calcium, ammonium, trialkylarylammonium, and tetraalkylammonium salts.

"Hydrate" as used herein refers broadly to the compound when the solvent is water, "Solvate" as used herein refers broadly is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, 1-propanol, 2-propanol, ethanol, methanol, DMSO, ethyl acetate, acetic acid, or ethanolamine.

Preferably, the compound decreasing the expression and/or activity of the chloride co-transporter NKCC1 has a low affinity for KCC2 (less than $10^{-7}$ or, preferably less than $10^{-8}$ M, more preferably less than $10^{-5}$ M) or at least a much higher affinity to NKCC1 than to KCC2 (of at least 2 orders of magnitude, preferably of at least 4 orders of magnitude, more preferably of at least 5 orders of magnitude and most preferably of at least 6 orders of magnitude higher binding constant (at least $10^{-9}$, preferably more than $10^{-10}$) or does nor bind to KCC2 at all. In particular, the NKCC1 antagonistic compound should not have any antagonistic effect on KCC2. More preferably the NKCC1 antagonistic compound should have an agonistic (i.e. reciprocal) effect on KCC2. Preferably, the compound decreasing the expression and/or activity of the chloride co-transporter NKCC1 is bumetanide or a derivative or analog thereof, as it specifically antagonizes NKCC1. In contrast, e.g. furosemide blocks both NKCC1 and KCCs with approximately equal potency and, thus, exerts simultaneously opposite effects on intracellular chloride levels, while bumetanide has a much higher affinity for NKCC1 than for KCC2 (Blaesse et al., 2009). Accordingly, compounds exerting less antagonistic effects on KCC2 or, even more preferably, exert agonistic effects on KCC2 thereby increasing its activity and/or expression (while simultaneously decreasing the expression and/or activity of NKCC1) are preferred according to the present invention.

Derivatives or analogs of any of the above compounds may be obtained by medicinal chemistry approaches, e.g. with increased lipophilicity or reduced diuretic effects. E.g. analogs of diuretics used as NKKC1 antagonists for treating tinnitus, e.g. analogs of bumetanide, furosemide, piretanide, azosemide, and torsemide, in particular analogs according to formula I will usually exhibit less diuretic effects than e.g. bumetanide, furosemide, piretanide, azosemide, and torsemide themselves.

Such analogs of known diurectics acting as NKCC1 antagonists and being useful for the treatment and/or prevention of tinnitus are defined by formulae II to VII Formula II

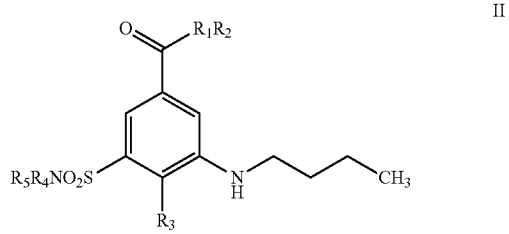

Formula III

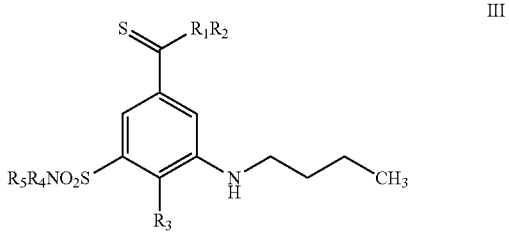

Formula IV

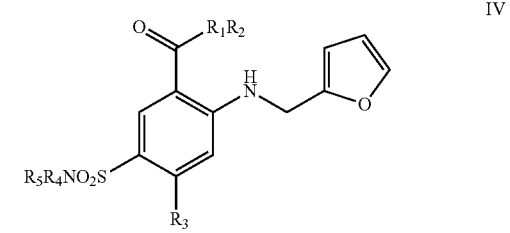

Formula V

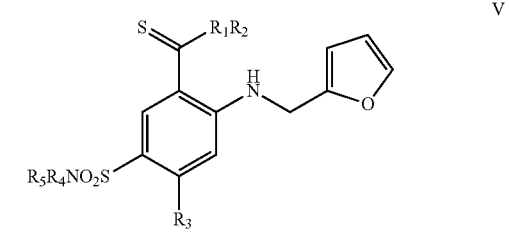

Formula VI

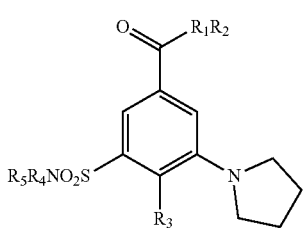

Formula VII

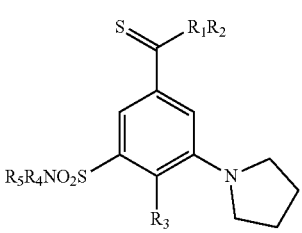

or a pharmaceutically acceptable salt, solvate, tautomer or hydrate thereof, wherein R1 is not present, H, O or S;

R2 is not present, H or when R1 is O or S, R2 is selected from the group consisting of hydrogen, alkyl, aralkyl, aryl, alkylaminodialkyl, alkycarbonylaminodialkyl, alkyloxycarbonylalkyl, alkylcarbonyloxyalkyl, alkylcarbonyloxyalkyl, alkylaldehyde, alkylketoalkyl, alkylamide, alkarylamide, arylamide, an alkylammonium group, alkylcarboxylic acid, alkylheteroaryl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted, and when R1 is not present, R2 is selected from the group consisting of hydrogen, N,N-dialkylamino, N,N-dialkarylamino, N,N-diarylamino, N-alkyl-N-alkarylamino, N-alkyl-N-arylamino, N-alkaryl-N-arylamino, unsubstituted or substituted;

R3 is selected from the group consisting of aryl, halo, hydroxy, alkoxy, and aryloxy, unsubstituted or substituted; and R4 and R5 are each independently selected from the group consisting of hydrogen, alkylaminodialkyl, carbonylalkyl, carbonylalkaryl, carbonylaryl, and salts thereof such as sodium, potassium, calcium, ammonium, trialkylarylammonium and tetraalkylammonium salts, Preferably with the following provisos: R3 of formula II is not phenyloxy when R1 is O and R2, R4 and R5 are H, more specifically, in some embodiments, the compound of formula II is not bumetanide; R3 of formula IV is not Cl, when R1 is O and R2, R4 and R5 are H, more specifically, in some embodiments, the compound of formula IV Is not furosemide; R2 of formula IV is not methyl when R1 is O, R3 Is Cl, and R4 and R5 are H, more specifically, in some embodiments, the compound of formula IV is not furosemide methyl ester; R3 of formula VI is not phenyloxy when R1 is O and R2, R4 and R5 are H, more specifically, in some embodiments, the compound of formula VI is not piretanide.

According to a preferred embodiment of the present invention, the compound of formula II can be bumetanide, bumetanide aldehyde, bumetanide methyl ester, bumetanide cyanomethyl ester, bumetanide ethyl ester, bumetanide isoamyl ester, bumetanide octyl ester, bumetanide benzyl ester, bumetanide dibenzylamide, bumetanide diethylamide, bumetanide morpholinoethyl ester, bumetanide 3-(dimethylaminopropyl) ester, bumetanide N,N-diethylglycolamido ester, bumetanide N,N-dimethylglycolamido ester, bumetanide pivaxetil ester, bumetanide propaxetil ester, bumetanide methoxy(polyethyleneoxy)$_{n-1}$-ethyl ester, bumetanide benzyltrimethylammonium salt and bumetanide cetyltrimethylammonium salt. In particular embodiments, the compound is not bumenatanide.

Alternatively, the compound of formula II can be bumetanide [—(C=O)—SH] thioacid, bumetanide S-methyl thioester, bumetanide S-cyanotnethyl thioester, bumetanide S-ethyl thioester, bumetanide S-isoamyl thioester, bumetanide S-octyl thioester, bumetanide S-benzyl thioester, bumetanide S-(morpholinoethyl) thioester, bumetanide S-[3-(dimethylaminopropyl)] thioester, bumetanide S-(N,N-diethylglycolamido) thioester, bumetanide S-(N,N-dimethylglycolamido) thioester, bumetanide S-pivaxetil thioester, bumetanide S-propaxetil thioester, bumetanide S-[methoxy(polyethyleneoxy)$_{n-1}$-ethyl] thioester, bumetanide [—(C=O)—S$^-$] benzyltrimethyl-ammonium thioacid salt and bumetanide [—(C=O)—S$^-$] cetyltrimethylammonium thioacid salt.

In some embodiments of the present invention, the compound of formula III can be metastable bumetanide [—(C=S)—OH] thioacid, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl thioester, bumetanide O-[3-(dimethylaminopropyl)] thioester, bumetanide O-(N,N-diethylglycolamido) thioester, bumetanide, O-(N,N-dimethylglycolamido) thioester, bumetanide O-pivaxetil thioester, bumetanide O-propaxetil thioester, bumetanide O-[methoxy(poryethyleneoxy)$_{n-1}$-ethyl]] thioester, bumetanide [—(C=S)—O$^-$] benzyltrimemylammonium thioacid salt and bumetanide [—(C=S)—O$^-$] cetyltrimethylammonium thioacid salt.

In some embodiments of the present invention, the compound of formula III can be bumetanide thioaldehyde, bumetanide [—(C=S)—SH] dithioacid, bumetanide methyl dithioester, bumetanide cyanomethyl dithioester bumetanide ethyl dithioester, bumetanide isoamyl dithioester, bumetanide octyl dithioester, bumetanide benzyl dithioester, bumetanide dibenzylthioamide, bumetanide diethylthioamide, bumetanide morpholinoethyl dithioester, bumetanide 3-(dimethylaminopropyl) dithioester, bumetanide N,N-diethylglycolamido dithioester, bumetanide N,N-dimethylglycolamido dithioester, bumetanide pivaxetil dithioester, bumetanide propaxetil dithioester, bumetanide methoxy (polyethyleneoxy)$_{n-1}$-ethyl dithioester, bumetanide benzyltrimethylammonium dithioacid salt and bumetanide cetyltrimethylammonium dithioacid salt.

In other embodiments of the present invention, the compound of formula IV can be furosemide, furosemide aldehyde, furosemide methyl ester, furosemide cyanomethyl ester, furosemide ethyl ester, furosemide isoamyl ester, furosemide octyl ester, furosemide benzyl ester, furosemide morpholinoethyl ester, furosemide 3-(dimethylaminopropyl) ester, furosemide N,N-diethylglycolamide ester, furosemide N,N-dimethylglycolamido ester, furosemide pivaxetil ester, furosemide propaxetil ester furosemide methoxy (polyethyleneoxy)$_{n-1}$-ethyl ester, furosemide benzyltrimethylammonium acid salt and furosemide cetyltrimethylammonium acid salt. In particular embodiments, the compound is not furosemide. In further embodiments of the present invention, the compound of formula IV can be furosemide [—(C═O)—SH] thioacid furosemide S-methyl thioester, furosemide S-cyanomethyl thioester, furosemide S-ethyl thioester, furosemide S-isoamyl thioester, furosemide S-octyl thioaster, furosemide S-benzyl thioester, furosemide S-(morpholinoethyl) thioester, furosemide S-[3-(dimethylaminopropyl)] thioester, furosemide S-(N,N-diethylglycolamido) thioester, furosemide S-(N,N-dimethylglycolamido) thioester, furosemide S-pivaxetil thioester, furosemide S-propaxetil thioester, furosemide S-[methoxy (poryethyleneoxy)$_{n-1}$-ethyl] thioester, furosemide [—(C═O)—S$^-$] benzyltrimethylammonium thioacid salt and furosemide [—(C═O)—S$^-$] cetyltrimethylammonium thioacid salt.

In other embodiments of the present invention, the compound of formula V can be metastable furosemide [—(C═S)—OH] thioacid, furosemide O-methyl thioester, furosemide O-cyanomethyl thioester, furosemide O-ethyl thioester, furosemide O-isoamyl thioester, furosemide O-octyl thioester, furosemide O-benzyl thioester, furosemide O-(morpholinoethyl) thioester, furosemide O-[3-(dimethylaminopropyl)] thioester, furosemide O-(N,N-diethylglycolamido) thioester, furosemide O-(N,N-dimethylglycolamido) thioester, furosemide O-pivaxetil thioester, furosemide O-propaxetil thioester, furosemide O-[methoxy (polyethyleneoxy)$_{n-1}$-ethyl] thioester, furosemide [—(C═S)—O$^-$] benzyltrimethylammonium thioacid salt an furosemide [—(C═S)—O$^-$] cetyltrimethylammonium thioacid salt.

In further embodiments of the present invention, the compound of formula V can be furosemide thioaldehyde, furosemide [—(C═S)—SH] dithioacid, furosemide methyl dithioester, furosemide cyanomethyl dithioester, furosemide ethyl dithioester, furosemide isoamyl dithioester, furosemide octyl dithioester, furosemide benzyl dithioester, furosemide dibenzylthioamide, furosemide diethylthioamide, furosemide morpholinoethyl dithioester, furosemide 3-(dimethylamino[rho]ropyl) dithioester, furosemide N,N-diethylglycolamido dithioester, furosemide N,N-dimethylglycolamido dithioester, furosemide pivaxetil dithioester, furosemide propaxetil dithioester, furosemide methoxy (polyethyleneoxy)$_{n-1}$-ethyl dithioester, furosemide benzyltrimethylammonium dithioacid salt and furosemide cetyltrimethylammonium dithioacid salt.

In still further embodiments of the present invention, the compound of formula VI can be piretanide, piretanide aldehyde piretanide methyl ester, piretanide cyanomethyl ester, piretanide ethyl ester, piretanide isoamyl ester, piretanide octyl ester, piretanide benzyl ester, piretanide dibenxylamide, piretanide diethylamide, piretanide morpholinoethyl ester, piretanide 3-(dimethylaminopropyl) ester, piretanide N,N-diethylglycolamide ester, piretanide dimethyglycolamide ester, piretanide pivaxetil ester, piretanide propaxetil ester, piretanide methoxy(polyethyleneoxy)$_{n-1}$-ethyl ester, piretanide benzyltrimethylammonium salt and piretanide cetyltrimethylammonium salt. In particular embodiments, the compound is not piretinide.

In some embodiments of the present invention, the compound of formula VI can he piretanide [—(C═O)—SH] thioacid, piretanide S-methyl thioester, piretanide S-cyanomethyl thioester, piretanide S-ethyl thioester, piretanide S-isoamyl thioester, piretanide S-octyl thioester, piretanide S-benzyl thioester, piretanide S-(morpholinoethyl) thioester, piretanide S-[3-(dimethylaminopropyl)] thioester, piretanide S-(N,N-diethylglycolamido) thioester, piretanide S(N,N-dimethylglycolamido) thioester, piretanide S-pivaxetil thioester, piretanide S-propaxetil thioester, piretanide S-[methoxy(polyethyleneoxy)$_{n-1}$-ethyl] thioester, piretanide [—(C═S)—S$^-$] benzyltrimethylammonium thioacid salt and piretanide [—(C═S)—S$^-$] cetyltrimethylammonium thioacid salt.

In further embodiments of the present invention, the compound of formula VII can be metastable piretanide [—(C═S)—OH] thioacid, piretanide O-methyl thioester, piretanide O-cyanomethyl thioester, piretanide O-ethyl thioester, piretanide O-isoamyl thioester, piretanide O-octyl thioester, piretanide O-benzyl thioester, piretanide O-(morpholinoethyl) thioester, piretanide, O-[3-(dimethylaminopropyl)] thioester, piretanide O-(N,N-diethylglycolamido) thioester, piretanide, O-(N,N-dimethylglycolamido) thioester, piretanide O-pivaxetil thioester, piretanide O-propaxetil thioester, piretanide O-[methoxy(polyethyleneoxy)$_{n-1}$-ethyl] thioester piretanide [—(C═S)—O$^-$] benzyltrimethylammonium thioacid salt and piretanide [—(C═S)—O$^-$] cetyltrimethylammonium thioacid salt.

In some embodiments, the compound of formula VII can be piretanide thioaldehyde, piretanide [—(C═S)—SH] dithioacid, piretanide methyl dithioester, piretanide cyanomethyl dithioester, piretanide ethyl dithioester, piretanide isoamyl dithioester, piretanide octyl dithioester, piretanide benzyl dithioester, piretanide dibenzylthioamide, piretanide diethylthioamide, piretanide morpholinoethyl dithioester, piretanide 3-(dimethylaminopropyl) dithioester, piretanide N,N-diethylglycolamido dithioester, piretanide N,N-dimethylglycolamido dithioester, piretanide pivaxetil dithioester, piretanide propaxetil dithioester, piretanide methoxy(polyethyleneoxy)$_{n-1}$-ethyl dithioester, piretanide benzyltrimethylammonium dithioacid salt and piretanide cetyltrimethylammonium dithioacid salt.

Alternatively, compounds having formula VIII are disclosed for use for the treatment and/or prevention of tinnitus:

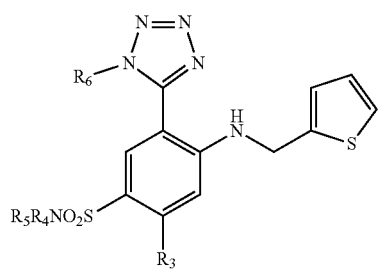

or a pharmaceutically acceptable salt, solvate, tautomer or hydrate thereof, wherein R3, R4 and R5 are defined above; and R6 is selected from the group consisting of alkyloxycarbonylalkyl, alkylaminocarbonylalkyl, alkylaminodialkyl, alkylthydroxy, a biocompatible polymer such as alkyloxy(polyalkyloxy)akylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted, preferably with the proviso that, in some embodiments, R3 of formula VIII is not Cl, when R4, R5 and R6 are H, more specifically, in some embodiments, the compound of formula VIII is not azosemide.

In certain embodiments, the compounds of formula VIII can be tetrazolyl-substituted azosemides (such as methoxymethyl tetrazolyl-substituted azosemides, methylthiomethyl tetrazolyl-substituted azosemides and N-mPEG350-tetrazolyl-substituted azosemides), azosemide benzyltrimethylammonium salt and/or azosemide cetyltrimethylammonium salt.

Other compounds for use for the treatment and/or prevention of tinnitus according to formula IX:

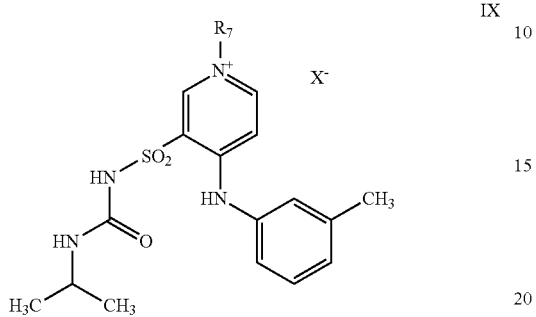

or a pharmaceutically acceptable salt, solvate, tautomer or hydrate thereof, wherein R7 is not present or selected from the group consisting of hydrogen, alkyloxycarbonylalkyl, alkylaminocarbonylalkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted; and X⁻ is a halide such as bromide, chloride, fluoride, iodide or an anionic moiety such as mesylate or tosylate; alternatively, X⁻ is not present and the compound forms an "inner" or zwitterionic salt (where R7 is H), preferably with the proviso that, in soma embodiments, R7 is always present and X⁻ is not present. More specifically, in some embodiments, the compound of formula IX is not torsemide.

In some embodiments, the compounds of formula IX can be pyridine-substituted torsemide quaternary ammonium salts or the corresponding inner salts (zwitterions). Examples include, but are not limited to, methoxymethyl pyridinium torsemide salts, methylthiomethyl pyridinium torsemide salts and N-mPEG350-pyridinium torsemide salts.

Definitions of substituents R1 to R7 are as defined above for formula I with the following additional definitions:

The term "amino" as used herein refers to —NH2 in which one or both of the hydrogen atoms may optionally be replaced by alkyl or aryl or one of each, optionally substituted.

The terms "alkylthio" or "thioalkyl" as used herein alone or as part of another group, refers to an alkyl group, as defined herein, appended to the parent molecular moiety through a sulfur moiety. Representative examples of alkylthio include, but are not limited to methylthio, thiomethyl, ethylthio, thioethyl, n-propylthio, thio-n-propyl, isopropylthio, thio-isopropyl, n-butylthio, thio-n-butyl and the like.

The terms "arylthio" or "thioaryl" as used herein refers to the group —ArS wherein Ar is aryl. Examples include, but are not limited to, phenylthio, thiophenyl, 2-naphthylthio and thio-2-napthyl.

The terms "alkarylthio" or "thioalkaryl" as used hereto refers to the group —S-alkyl-aryl wherein Ar is aryl. Examples include, but are not limited to, benzylthio, thiobenzyl, 2-naphthylthio and thio-2-naphthyl.

The term "quaternary ammonium" as used herein refers to a chemical structure having four bonds to the nitrogen with a positive charge on the nitrogen in the "onium" state, i.e., "R4N" or "quaternary nitrogen," whereto R is an organic substituent such as alkyl or aryl. The term "quaternary ammonium salt" as used herein refers to the association of the quaternary ammonium cation with an anion.

Alternatively, this compound decreasing the expression and/or activity of chloride co-transporter NKCC1 may also be preferably selected from non-diuretic compounds, such as protein kinase inhibitors staurosporine and K252a, through SPAK autophosphorylation and substrate phosphorylation of the co-transporter, or the sulfhydryl agents N-ethylmaleimide (NEM) and diamide (Gagnon et al., 2006).

In an alternative embodiment, NKCC1 antagonistic compounds, which (i) decrease expression and/or activity of the chloride co-transporter NKCC1 and (ii) additionally modulate chloride co-transporter KCC2 such that the KCC2 expression and/or activity level increases (KCC2 agonistic), are disclosed as well. Such compounds act preferably in sensorineural structures of the auditory system, more preferably, in cochlear hair cells, spiral ganglion neurons, satellite glial cells or other glial or neural cells along the auditory pathway. Compounds exerting both effects NKCC1 antagonistic and KCC2 agonistic) are preferably selected from the group consisting of CCC-interacting protein (C1P1), protein phosphatase PP1, NEM (N-ethylmaleimide) and staurosporine.

Intracellular chloride levels may be decreased through administration of CCC (cation chloride co-transporter)-interacting protein (C1P1) or a peptide (with a length of typically between 10 and 50 amino acids) derived therefrom exhibiting the NKCC1 antagonistic and KCC2 agonistic properties of full-length C1P1, which was shown to inhibit NKCC1 and activate reciprocally KCC2 (Wenz et al., 2009). In addition, it is known that protein phosphatase PP1 deactivates NKCC1 and activates KCC2. Similar synergistic effects have been reported with NEM (N-ethylmaleimide) and staurosporine, which are within the scope of the present invention as well.

Antagonistic NKCC1 antibodies or antagonistic NKCC1 epitop recognizing fragments of antibodies, e.g. Fab, F(ab)₂, diabodies, scFv, Fv, and minibodies, binding to NKCC1 and blocking or decreasing its activity may be used within the scope of the present invention as well. Antibodies may also be provided in humanized form.

In terms of NKCC1 antagonistic compounds, decreasing the expression level, NKCC1 may be suppressed by siRNA or shRNA specifically binding to segments of the NKCC1 mRNA, siRNA typically has a length of 21 to 23 nucleotides being complementary to a region on the NKCC1 mRNA. Ribozymes specifically recognizing a target region on the NKCC1 mRNA may be used as well to antagonize the NKCC1 expression level. Furthermore, such compounds may be antisense RNA binding to the NKCC1 mRNA and thereby blocking its translation, e.g. antisense oligonucleotides. Alternatively, the NKCC1 expression level may be reduced by compounds acting directly on the subscription of the NKCC1 gene in the relevant cells of the auditory system. Such compounds may e.g. interfere with regulatory regions of the NKCC1 gene, e.g. by blocking the promoter activity or by blocking transcription factors required for the NKCC1 gene to be transcribed.

Preferably, any NKCC1 antagonistic compound which may indirectly exert an effect on the up-regulation of KCC2 due to its effect on NKCC1 should not result in an overexpression, or over-activity beyond the physiological level of KCC2 in healthy cells in order to avoid potential adverse effects which may drive the cells into e.g. cell death.

In a preferred embodiment of the present invention, the compound modulating chloride cotransporter NKCC1 is not interfering with the auditory function, i.e. hearing, or only in a clinically insignificant and/or reversible fashion. As $Cl^-$ is one of the major biological ions involved in various physiological and pathophysiological processes, any modulation of chloride levels for the purpose of attenuating tinnitus may potentially interfere with ionic homeostasis, in the auditory system and in particular in the cochlea. Changes in intracochlear chloride levels may induce changes also in $Na^+$ or $K^+$ levels. Selection and dosing of the inventive compounds will preferably be selected such that the administration of that compound will not impact the endolymphatic potential and hearing function.

In a second aspect, the present invention concerns a pharmaceutical composition comprising, as an active agent, a compound modulating chloride co-transporter NKCC1 according to the present invention. Such pharmaceutical compositions of the invention, at least one compound or pharmaceutically acceptable salts thereof as the active ingredient is intimately mixed with appropriate carriers and additives according to techniques well known to those skilled in the art of pharmaceutical formulations, Remington. The Science And Practice of Pharmacy, 20th Edition, (Gennaro, A. R., Chief Editor), Philadelphia College of Pharmacy and Science, 2000, which is incorporated by reference in its entirety.

Such a pharmaceutical composition according to the invention will typically contain "carrier materials" which are excipients that are compatible with an active agent disclosed herein, the targeted ear structure(s) and the release profile properties is acceptable for pharmaceutical formulations to be administered to the ear.

Such carrier materials include, e.g., binders, suspending agents, disintegration agents, filling agents, surfactants, solubilizers, stabilizers, lubricants, wetting agents, diluents, and the like. Ear-compatible pharmaceutical carrier materials" include, but am not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidyicholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute an active agent disclosed herein prior to delivery and which are compatible with the targeted auris structure(s). "Dispersing agents," and/or "viscosity modulating agents" are materials that control the diffusion and homogeneity of an active agent disclosed herein through liquid media. Examples of diffusion facilitators/dispersing agents include but are not limited so hydrophilic polymers, electrolytes, Tween 60 or 80, PEG, polyvinylpyrrolidone (PVP; commercially known as Plasdone-), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose, phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68, F88, and F108, which are block copolymers of ethylene oxide and propylene oxides); and poloxamines (e.g., Tetronic 908, also known as Poloxamine 908, which is a tetrafunctional block copolymer derived from sequential addition of propylene oxide and ethylene oxide to ethylenediamine (BASF Corporation, Parsippany, N.J.)), polyvinylpyrrolidone Ki 2, polyvinylpyrrolidone Ki 7, polyvinylpyrrolidone K25, or polyvinylpyrrolidone K3 0, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose; methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Optional dispersing agents useful in liposomal dispersions and self-emulsifying dispersions of an active agent disclosed herein disclosed herein are dimyristoyl phosphatidyl choline, natural phosphatidyl choline from eggs, natural phosphatidyl glycerol from eggs, cholesterol and isopropyl myristate. Anionic, non-sulfated glycosaminoglycans are also preferred, in particular hyaluronate/hyaluronic acid which is a polymer of disaccharides, themselves composed or D-glucuronic acid and D-N-acetylglucosamine, linked via alternating β-1,4 and β-1,3 glycoside bonds may be used as well. Preferably, the molecular weight of hyaluronate/hyaluronic acid is in the range of 50,000 to 5,00,000 Da.

"Solubilizers" refers to ear-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpynolidone, polyvinylpyrrolidone, hydroxypropylmethyl cellulose, hydroxypropyl cyclodextrins, ethanol, n-butanol, isopropyl alcohol, cholesterol bile salts, polyethylene glycol 200-600, glycofurol, transcutol propylene glycol, and dimethyl isosorbide and the like.

"Stabilizers" refers to compounds such as any antioxidation agents, buffers, acids, preservatives and the like that are compatible with the environment of the targeted auris structure. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Surfactants" refers to compounds that are ear-acceptable, such as sodium lauryl sulfate, sodium docusate, Tween 60 or 80, triacetin, vitamin E TPGS, sorbitan monooleate, polyoxyethylene sorbitan monooleate, polysorbates, poloxamers, bile salts, glyceryl monostearate, copolymers of ethylene oxide and propylene oxide, e.g., Plutonic (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The composition may preferably-comprise polymers of synthetic or natural origin, which are preferably biocompatible. These polymers may include controlled release polymers. In case the composition is provided as a gel, gel forming polymers are preferred, e.g. hyaluronic acid resp. hyaluronates, lecithin gels, (poly)alanine derivatives, pluronics, poly(ethyleneglycol), poloxamors, chitosans, xyloglucans, collagens, fibrins, polyesters, poly(lactides), poly(glycolide) or their co-polymers PLGA, sucrose acetate isobutyrate, and glycerol monooleate. Other ingredients may be carriers, e.g. wafer for liquid formulations, oil-in-water formulations, water-in-oil formulation. Additionally, the pharmaceutical may comprise viscosity enhancing or decreasing agents. The formulation may be based on microspheres, microparticles, liposomes, nanocapsules, nanospheres, or nanoparticles.

Preferably, the pharmaceutical composition is administered systemically, e.g. by an oral dosage form, by intramuscular or intravenous routes, or, preferably, a dosage form is provided suitable to be administered topically or locally or in the ear. More preferably, the pharmaceutical composition is a dosage form suitable to be administered locally on or in the ear, in particular onto the round window or oval window of the inner ear, i.e. the middle ear/inner ear interface. Local administration is particularly adequate, preferably to the round window of the inner ear, as KCC2 expression during tinnitus is reduced in the auditory system, whereby inner hair cells, auditory nerve and spiral ganglia neurons or its peripheral and central projections are primarily affected. In some embodiments the delivery system comprises a syringe and needle apparatus that is capable of piercing the tympanic membrane and directly accessing the round window membrane of the auris. In some embodiments, 0.2 to 0.5 ccs of a composition disclosed herein is injected into the middle ear for diffusion across the round window membrane and/or the oval window. In some embodiments, the composition is delivered into the middle ear via a paracentesis, a tympanometal flap, or through a ventilating tube. A composition disclosed herein may e.g. also be administered directly into the inner ear, e.g. via an incision in the stapes footplate or a composition disclosed herein may be administered to the cochlea via a cochleostomy. A composition disclosed herein may also e.g. be administered to the vestibular apparatus (e.g., semicircular canals or vestibule).

A dosage form suitable to be administered locally on or in the ear has the advantage that the substance is administered in a targeted manner at the site of action, so that minor amounts of active substance are required for obtaining therapeutic success. The stress on the remainder of the treated patient's body is thus less, and side effects are substantially reduced.

Such a pharmaceutical composition according to the invention may be administered locally by microcatheters e.g. implanted into the patient, micrometering systems, (micro)wicks, or intratympanic infections, cochlear implants, a pump device, an infusion pump or intracochlear delivery via injection, perfusion, etc.

For local administration, it will he provided in a liquid, semi-liquid or viscous form. It may preferably be provided as a gel, in particular with a hydrogel based carrier matrix, a cream, paint, foam, or an ointment. Accordingly, it may be e.g. provided in the form of a hydrogel, in situ forming spongy material, actinic radiation curable gel or thermoreversible gel. In one embodiment, the composition may be provided as a controlled release formulation.

A gel-like foundation is preferred to ensure retention of the composition in the middle ear, respectively on the round or oval window membranes, even in case of openings of the Eustachian tube e.g. due to swallowing. Gels include a single-phase or a two-phase system. A single-phase gel consists of organic macromolecules distributed uniformly throughout a liquid in such a manner that no apparent boundaries exist between the dispersed macro-molecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles. Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions disclosed herein is pseudo plastic, plastic, thixotropic, or dilatant. In some embodiments the enhanced viscosity ear-acceptable formulation described herein is not a liquid at room temperature. In certain embodiments, the enhanced viscosity formulation is characterized by a phase transition between room temperature and body temperature. In some embodiments, the phase transition occurs at 1 [deg.])C. below body temperature, at 2 [deg.]C. below body temperature, at 3 [deg.]C. below body temperature, at 4 [deg.]C. below body temperature, at 6 [deg.]C. below body temperature, at 8 [deg.]C. below body temperature, or at 10 [deg.]C. below body temperature.

The pharmaceutical composition according to the present invention comprises, as an active agent, preferably a compound moderating NKCC1 activity and/or expression. In particular by antagonizing its activity and/or expression. Due to that antagonistic effect on NKCC1 the pharmaceutical composition according to the present invention will preferably increase activity and/or expression or KCC2. That increase in activity and/or expression of KCC2 is thus an indirect effect of the NKCC1 antagonistic compound of the invention.

In one preferred embodiment the pharmaceutical composition according to the present invention further comprises, as an additional active agent, a GABAergic agonist and/or a glycine agonist. In such a case, the compound modulating chloride co-transporter NKCC1 according to the present invention is used in the treatment or prevention of acute or chronic tinnitus together with one or more GABAergic agents and/or one or more glycine agonists. Such a combination may be provided as a combination therapy (administering the NKCC1 antagonist and other active agents separately) or may be formulated by one single formulation provided herein as pharmaceutical composition. In case the agents are formulated separately, they may be provided as a kit together with therapy information leaflet. Administration of the agents of the combination therapy may be carried out simultaneously, preferably subsequently as defined by a staggered treatment protocol. Co-administration of a GABA and/or glycine agonist together with an antagonistic NKCC1 compound according to the invention may yield a synergistic treatment effect as the antagonist may block the excitatory effect of the agonist.

Preferably, the GABAergic or glycine agonist used in such a pharmaceutical composition of the invention or in such a combination therapy is selected from the group consisting of midazolam, diazepam, flurazepam, oxazepam, nitrazepam, flunitrazepam, clonazepam, triazolam, clobazam and brotizolam, baclofen, gamma-vinyl-GABA, gamma-acetylene-GABA, progabide, muscimol, iboten, sodium valproate or tetrahydroisoxazolopyridine (THIP).

In another aspect, the present invention is related to a method for treatment or prevention of acute or chronic, preferably chronic tinnitus comprising a therapeutically effective amount of a compound modulating chloride co-transporter NKCC1 according to the present invention or a pharmaceutical composition according to the present invention. Preferably, the method for treatment or prevention of acute or chronic tinnitus according to the present invention, relates to the administration, in a systemic or local administration mode, of compounds that decrease the intracellular level of chloride in a sensorineural structure of the auditory system by antagonizing NKCC1 to attenuate tinnitus. In order to achieve such on effect, the disclosed antagonistic compounds may modulate the function or expression of the chloride co-transporter NKCC1 in cochlear hair cells, spiral ganglia neurons, glial satellite cells or other glial and neural cells along the auditory pathway. As a second, indirect effect of these compounds, inhibiting the activity or expression of NKCC1 may preferably result in an up-regulation of activation and expression of KCC2.

In a preferred embodiment, the method of treatment comprises administering systemically or locally on or in the ear. The compounds of the invention may eventually be administered in combination with other compounds relying on distinct mechanisms of action, e.g. GABAergic or glycinergic compounds as described above.

Another aspect of the present invention relates to a screening method for the identification and characterization of compounds capable of modulating chloride a co-transporter, e.g. NKCC1 or KCC2, preferably, of antagonizing NKCC1 activity and/or expression and thereby increasing NKCC2 expression and/or activity. A screening method for the identification of compounds usable for the present invention may be carried out by determining down-regulation/loss of activity of NKCC1 or, preferably, by determining increase in expression and/or activity of KCC2. Such an assay for determining the test compound's inhibitory potential on e.g. KCC2 expression/activity may include the selection of an indicator molecule, e.g. a radioactive indicator ion (e.g. $^{86}Rb^+$, $Cs^+$). Indicators may be based on a radioactive label or, preferably, cations transported through the channels may be detected by a fluorescence label binding to such a cation. Such a fluorescence label may he a BTC-AM dye, whereby the association of cation and fluorescence label may cause a fluorescence change that can be detected. Such a cation, which may bind to a BTC-AM dye, may e.g. by $Tl^+$. Thereafter, such an indicator may be used to measure the flux (e.g. of the cation) (into and/or out of the cell), typically into the cells. The cationic indicator should be selected such that it is co-transported across the cell membrane with $Cl^-$ by the chloride co-transporter protein. In case of measuring the transporter activity of bidirectional transporter ability (such as e.g. for KCC2) the direction of transport depends on the existing ion gradient. By exogenously adding the cations to the cell suspension, typically the influx (into the cells) is measured by such an assay format, e.g. for KCC2.

Accordingly, the present invention provides a screening method for the identification and characterization of compounds capable of modulating one or more chloride transporters, by (a) providing cells stably expressing the one or more chloride transporters, (b) adding a test compound to the cells, (c) adding a transporter cation and (d) measuring the cation transport across the cell membrane.

Cells to be used for such an assay may be human cell lines (e.g. HEK293 cells), preferably stably expressing recombinant human KCC2 and/or NKCC1 in a heterologous way.

In this regard, cells are typically plated and the indicator is loaded onto the cells. The cells may be washed thereafter, e.g. in an assay buffer (e.g. HEPES buffer) and loaded onto the measuring device, e.g. a FLIPR (Fluorimetric imaging Plate Reader). The test candidate compounds to be screened are thereafter loaded onto the cells, incubated for a short period of time (e.g. 1 to 10 min) and, thereafter, data acquisition starts by adding the cation, which is typically dissolved, e.g. in an assay buffer. TlNO3 may be used as a salt which contains $Tl^+$ as a cation.

The read-out of the cation transport is carried out, e.g. by measuring the fluorescence signal (e.g. by a FLIPR device). The fluorescence emission signals are under such conditions measured for typically 1 to 10 min. The initial rate of transport, for e.g. $Tl^+$ transport, is typically deduced from the analysis of the linear increase of fluorescent signals within e.g. the initial 30 s or, preferably, 10 s following the addition of the cation. Data analysis may be carried out by a calculation based on the measured signal for (e.g. relative $Tl^+$) initial transport rates as a percentage of the control. Typically, the measurement results in a curve starting with a strong increase, followed by a phase of continuously slower increase and typically ends in a plateau phase. The calculation of the channel transporter activity may reliably be measured by the initial rate of cation transport (initial linear phase of the signal increase). The difference of transporter activity upon addition of test candidate compounds (as compared to a setup of the method without the addition of a test candidate compound) may be determined (higher or lower initial rate of cation channel transport) may allow to conclude whether a compound may be categorized as a positive modulator or an inhibitory modulator. Concentration dependency of the modulator may be assessed as well.

In a preferred embodiment, the screening assay may be carried out by blocking specific channels potentially interfering with the screening method due to co-transporter activity. If e.g. KCC2 activity shall be avoided, the assay may be carried out by (specifically) blocking e.g. KCC2 activity. Blocking KCC2 activity may be achieved by adding KCC2 inhibitors to the assay system, e.g. furosemide or alkanoic acid DIOA.

Accordingly the screening method of the invention may additionally encompass one or more of the following steps: (i) provision of cells with heterologous expression of one or more of the transporters, (ii) additionally adding a fluorescence dye binding to the transporter cation, (iii) measuring the initial cation transport rate and (iv) blocking interfering transporter activity of another transporter by e.g. adding an inhibitor of that other transporter.

In one preferred embodiment, the screening method of the present invention comprises the step of determining whether a candidate compound is capable of modulating intracellular chloride levels in a cell by modulating activity and/or expression of one or more chloride co-transporters, and in turn is useful for the prevention and treatment of tinnitus.

The screening method of the present invention may comprise assaying a chlorine transporter gene expression, e.g. KCC2, in the presence versus the absence of a test compound. Such gene expression may be measured by detection of the corresponding RNA or protean, or via the use of a suitable reporter construct comprising a transcriptional regulatory element, normally associated with such a chloride transporter or KCC2 gene, operably-linked to a reporter gene. Positive modulators of KCC2 may e.g. be identified by high-throughput screening such as proposed by Zhang et al., 2010, using a fluorescence-based thallium transport assay with a Fluorometric Imaging Plate Reader.

EXAMPLES

Example 1

Objective

Figure 1:
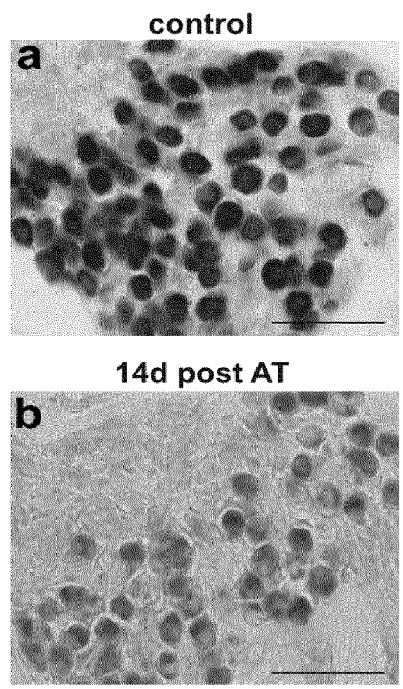
FIG. 1 shows that tinnitus inducing acoustic trauma (120 dB at 10 kHz for 2 hours) leads to a reduced KCC2 expression in inner hair cells and spiral ganglion neurons of the rat.
- A) In situ hybridization of spiral ganglion neurons at the midbasal turn of cochleae. 14 days after exposure a clear down-regulation of KCC2 mRNA in the noise exposed animal (AT) is observed (b). Comparison with the sham exposed control animal is provided by (a).
- B) Western Blot of KCC2. The first lane shows hippocampus tissue as a positive control with a clear band at 140 kDa, which KCCC2. The second lane corresponds to the cochlear tissue of a non-exposed control animal, the third lane to cochlear tissue of a noise exposed animal 7 days after exposure. A clear down-regulation of KCC2 protein can be seen In the noise exposed animal (right lane) compared to the control animal.
Figure 1:
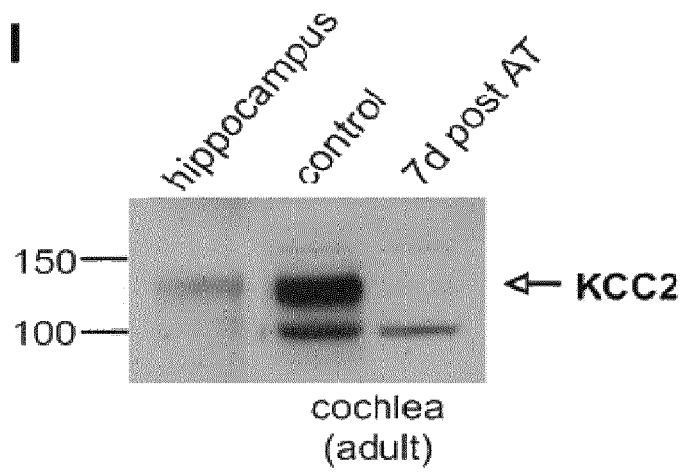

The loop diuretic furosemide has been proposed as a (reversible) treatment of tinnitus. It has been hypothesized that it attenuates the firing of the auditory nerve by reducing the endocochlear potential (Risey et al., 1995). Yet, concurrently tinnitus is also known as a side effect of furosemide. The inventors sought to elucidate whether and, if yes, bow the expression of chloride co-transporters in the cochlea changed following an insult to the cochlea susceptible of inducing tinnitus in order to identify starting points for the development of a novel pharmacotherapy for tinnitus.

Materials and Methods 13 anaesthetized adult female Wistar rats were exposed for 2 hours intra-aurally to a continuous 10 kHz tone at an intensity of 120 dB SPL in a sound attenuation booth. This exposure is susceptible of inducing tinnitus in rats (e.g. Tan et al., 2007). The acoustic stimulus was calibrated at the head level of the animal. Four anaesthetized control animals were placed in the sound attenuation booth for the same duration, but the speaker remained turned off. 14 days after the real or sham sound exposure annuals were sacrificed. The cochleae were harvested and fixed by immersion in 2% paraformaldehyde (PFA), 125 mM sucrose in 100 mM phosphate buffered saline (PBS), pH 7.4, for 2 hours. They were decalcified in Rapid Bone Decalcifier (Eurobio, Les Ulis Cedex, France) followed by an overnight incubation in Hanks buffered saline with 25% sucrose. The next day cochleae were embedded in O.C.T. compound (Miles Laboratories, Elkhart, Ind., USA). Before use, tissue samples were cryosectioned at 10 μm thickness for in situ hybridization as well as immunohistochemistry, mounted on SuperFrost®/plus microscope slides and stored at −20° C.

For immunohistochemistry slides were dried at room temperature for 30 minutes. Afterwards, they were permeabilized for 3 minutes with PBS+0.1% Triton, washed with PBS and blocked with 1% BSA/PBS. Slides were incubated over night with primary antibody diluted in 0.5% BSA/PBS (KCC2 1; 150, Upstate Biotechnology, Hamburg, Germany). On the next day slides were washed with PBS and incubated with secondary antibody (Cy3-anti-rabbit, Jackson Immuno Research, Suffolk, UK) for 1 hour. Slides were washed again and mounted with VECTASHIELD® containing DAPI (Vector Laboratories, Burlingame, Calif., USA). Slides were viewed using an Olympus AX70 microscope.

For in situ hybridization slides were incubated with anti-digoxigenin antibody conjugated to alkaline phosphatase (1:750, Roche, Mannheim, Germany). The sections were then allowed to develop in the substrate solution containing nitroblue tetrazolium salt and 5-bromo-4-chloro-3-indolyl phosphate (Sigma, Munich, Germany). The sections were observed at different time periods to monitor the development of the substrate into a colored product. Sections from controls and exposed animals ware stopped at the same time, mounted and viewed using an Olympus AX70 microscope.

For Western Blot analysis proteins from rat cochleae and brain tissue were separated by SDS polyacrylamide gel electrophoresis sing the XCell Sure Lock Mini Cell and NuPage Novex 4-12% Bis-Tris Gels (Invitrogen, Karlsruhe, Germany) according to the manufacturer's instructions. For immunoblotting, proteins (40 µg/lane) were transferred onto polyvinylidine difluoride transfer membranes using the Xcell II Blot Module (Invitrogen). The KCC2 antibody (Blaesse et al., 2006; generously provided by H G Nothwang and E Friauf) was preincubated overnight at 4° C., in a reasonable dilution. Bound antibody was visualized with the Enhanced Chemiluminescence Plus Western Blotting Detection Reagent (Amersham Biosciences, Freiburg, Germany). For quantification, densitometric analysis was performed using the Cell^F software (Olympus, Hamburg, Germany). The intensity of the control band and the band from the exposed tissue were measured and compared against each other.

Results

Animals exposed to excessive noise that is susceptible of inducing tinnitus showed a clear down-regulation of KCC2 14 days after noise exposure (FIG. 1a). Immunohistochemistry showed a markedly reduced expression of the KCC2 protein in inner hair cells compared to non-exposed control animals. In situ hybridization revealed also a clear down-regulation of KCC2 mRNA in spiral ganglion neurons of noise exposed cochleae compared to non-exposed cochleae. Western Blots showed a clear down-regulation of KCC2 protein in cochlear tissue of noise exposed animals compared to control animals (7.8 times lower) as shown by FIG. 1b. The results from this experiment showed for the first time that KCC2 is down-regulated following a cochlear insult such as acoustic trauma. Whether this down-regulation is related to hearing loss, to tinnitus or both, remained to be elucidated as a result of that experiment. Accordingly Example 2 was set up for further elucidation.

Example 2

Objective

The aim of the 2nd experiment was to assess whether down-regulation of KCC2 observed in the first experiment was related to the pathophysiology of hearing loss or to that of tinnitus, or to both. This down-regulation could suggest that tinnitus induction by furosemide may be related to its known effect on KCC2, rather than through its attenuation of the endocochlear potential, as commonly suspected (e.g. Risey et al., 1995). For this purpose, a behavioural model as described by Rüttiger et al., 2003 was used to discriminate between animals with and without tinnitus.

Materials and Methods 36 adult female Wistar rats were trained in a conditioning chamber to actively access a liquid feeder whenever a constant sound was present. During silence, no reward was given. The conditioning was completed when animals performed more accesses to the reward feeder during periods of sound than during periods of silence.

On Day 0 conditioned rats were anaesthetized and exposed intra-aurally either for 1 hour (Group A; n=18) or for 1.5 hours (Group B; n=18) to a continuous 10 kHz tone at an intensity of 120 dB SPL in a sound attenuation box. The acoustic stimulus was calibrated at the head level of the animal. All animals were divided into groups corresponding to their tinnitus behaviour: in Group A, 5 animals exhibited tinnitus, 10 no tinnitus, and 3 died, while in Group B 5 animals developed tinnitus, 12 no tinnitus, and 1 died. Group A animals were sacrificed 6 days and Group B animals 30 days after the real or sham sound exposure.

Tissue preparation, immunohistochemistry and in situ hybridization were carried out as described for Example 1.

Ribbon synapses of inner hair cells were counted. Sections were viewed using an Olympus AX70 microscope equipped with epifluorescence illumination (100× objective, NA=1.35) and a motorized z-axis. Images were acquired using a CCD camera and the imaging soft-ware Cell^F (OSIS GmbH, Münster, Germany). For Otoferlin and CtBP2/RIBEYE immunopositive spot counting on cryosectioned cochleae were performed through imaging over a distance of 8 µm with the complete coverage of the IHC nucleus and beyond in an image-stack along the z-axis (z-stack). Typically z-stacks consisted of 30 layers with a z-increment of 0.276 82 m, for each layer one image per fluorochrome was acquired. Z-stacks were 3-dimensionally deconvoluted using Cell^F's RIDE module with the Nearest Neighbour algorithm (OSIS GmbH, Müster, Germany).

Results

Figure 2:
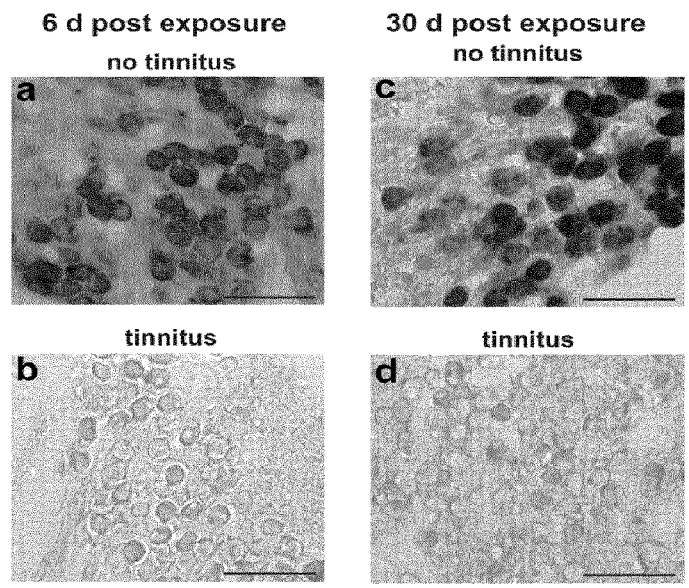
FIG. 2 shows that down-regulation of KCC2 in rat inner hair cells and spiral ganglion neurons at the cochlear midbasal turn 6 or 30 days following noise trauma (120 dB at 10 kHz for 1 hour respectively 1.5 hours) is inherent to the pathophysiology of tinnitus and not related to hearing loss.
- A) In situ hybridization of spiral ganglion neurons at the midbasal turn of cochleae, 6 days after noise trauma a clear down-regulation of KCC2 mRNA in the animal showing tinnitus behaviour is observed (a) compared with the animal that shows no tinnitus behaviour (b). The same observation is made 30 days post noise trauma (c) and (d).
- B) Count of inner hair cell ribbon synapses (as % of control) 2 weeks following noise exposure of rat cochleae. A significant decrease of ribbons was observed in noise exposed animals showing tinnitus behavior, in the midbasal (middle columns) and basal (right columns) cochlear turns, in comparison to animals exposed to the same noise, but not showing tinnitus behavior.
Figure 2:
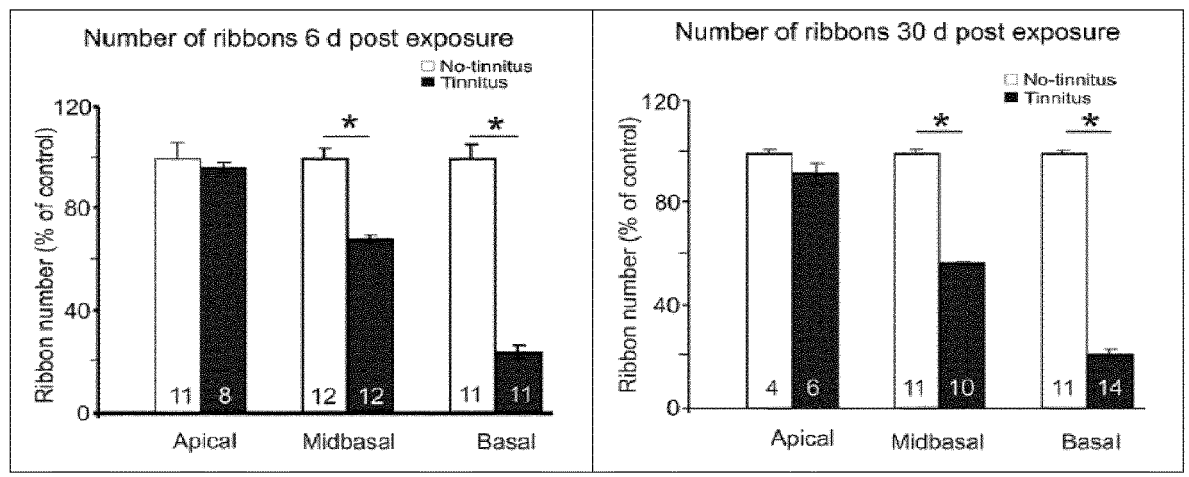

In both Group A and Group B KCC2 was markedly down-regulated 6 days or 30 days after noise exposure in those animals showing the behavioural correlate of tinnitus compared with animals displaying no tinnitus behaviour (as shown in FIG. 2a). Immunohistochemistry shows a clearly reduced expression of the KCC2 protein in inner hair cells of tinnitus animals compared to non-tinnitus animals. In situ hybridization reveals also a clear down-regulation of KCC2 mRNA in spiral ganglia neurons of tinnitus animals compared to non-tinnitus cochleae. Further, IHC ribbons of hearing impaired tinnitus animals were significantly reduced in the midbasal and basal turns in comparison to no tinnitus animals (n=4 animals, p<0.001 for the two-way ANOVA, and p<0.02 for the post-test two-sided Student's t-test, both with $\alpha$=0.05) (see FIG. 2b).

In conclusion, the results from Example 2 showed for the first time ever that down-regulation of KCC2 in inner hair cells and spiral ganglion neurons following noise trauma is not related to hearing loss, but rather inherent to the pathophysiology of tinnitus. This finding suggests that tinnitus induction by diuretics, such as furosemide acting on NKCC1 and KCC2, is likely the result of KCC2 inhibition, whereas their contrary effect is typically due to its NKCC1 antagonism at different concentrations. As a consequence, a strategy for tinnitus treatment consists of -down-regulating NKCC1 in order to lower intracellular $Cl^-$ levels.

Example 3

Objective

The aim of the third experiment was to assess whether pharmacological modulation of intracellular chloride levels in the cochlea following tinnitus-inducing noise trauma can suppress tinnitus. Since bumetanide has a much higher affinity for NKCC1 than for KCC2 (Payne et al., 2003), its administration should—in view of the previous findings of the present invention—allow for reducing intracellular $Cl^-$ levels as the inhibitory effect on NKCC1 would dominate any—undesired—inhibitory effect on KCC2.

Materials and Methods 20 adult female Wistar rats were anaesthetized as described above for the previous experiments. First, auditory brainstem response (ABR) measurements were performed. As in Experiment 2, they were then exposed in a sound attenuation booth for 1.5 hours to a continuous 10 kHz tone at an intensity of 120 dB SPL (Group A; n×10) or sham exposed in the same setting (Group B; n=10).

Animals were treated bilaterally right after noise trauma with either artificial perilymph (AP) or bumetanide (Sigma B3023, Lot 027Ko988). AP was prepared freshly in accordance with Guitton et al., 2003 (140 mM NaCl, 4 mM KCl, 2 mM $CaCl_2$, 2m M $MgCl_2$, 10 mM glucose, 10 mM HePES). Bumetanide (300 μM) was prepared as follows: 50 mg of bumetanide powder was diluted in 6.87 ml AP. This 20 mM stock solution was diluted 1:66 in AP (15.15 μL stock solution and 984.85 μL AP). 5 animals of Group A and 5 animals of Group B received AP (total 10 animals) and 5 animals of Group A and 5 animals of Group B received bumetanide total (10 animals).

For the local treatment administration, the fur was removed behind the ears and the bulla exposed in a retro-auricular approach. A small hole was carefully drilled into the bony bulla just above the round window niche (0.6-1 mm in diameter). The mucosa was opened and the region around the round window carefully dried of fluid. Through the hole, a small gel-foam pellet (Gelita Tampon; Braun, Melsungen, Germany) was inserted into the round window niche, 5-8 μl of bumetanide solution or AP were applied on the gel foam by means of a precision pipette with gel loader tips, thus avoiding air bubbles under the gel. Visual inspection showed that the niche was completely filled and covered with the gel. The hole in the bulla was then covered from the outside with muscular tissue and the wound was sutured with surgical thread (Vicryl, Johnson & Johnson, Norderstedt, Germany). Postoperatively the animals were kept warm with the body temperature being controlled until wake-up.

For ABR measurements only Dormitor was given as anesthetic. 15 minutes prior to surgery, Fentanyl was given additionally subcutaneously (s.c.). After the surgery Rimadyl s.c. was given as analgesic. After letting the animals sleep for several hours, the effect of Dormitor was antagonized by Antisedan s.c.

Total RNA was isolated as previously described (Tan et al., 2007) using the Qiagen Rneasy Mini Kit (Qiagen, Hilden, Germany). In brief, tissue was lysed using lysate buffer mixed with β-mercaptoethanol. After three freeze-thawing steps samples were centrifuged and the supernatant kept for further cleaning steps with washing buffer. RNA was eluted in 40 μl RNase free water. Total RNA was transcribed into cDNA as previously described (Tan et al., 2007) using the Sensiscript RT Kit (Qiagen). In brief, 50 ng of RNA were incubated 10 min at 65° C. with RNase free water and Oligo dT15 Primers. After adding RNAsin and the Sensiscript enzyme samples were incubated for 1 hour at 37° C. For the real-time PCR reaction 12.5 μl of SYBRGreen (QuantiFast Sybr Green, Qiagen), 1 μl Primer Mix, 7.3 μl ddH2O and 4 μl cDNA were used per well. All samples were run in triplicate for every primer used as well as for the negative control (no cDNA added), 18S rRNA and β-actin were used as housekeeping genes.

Immunohistochemistry was carried out as described above. Ribbon synapses of inner hair cells were counted as in Experiment 2.

ABRs were recorded in anesthetized animals as previously described (Knipper et al., 2000, Schimmang et al., 2003). In short, electrical brainstem responses to free field click (100 μs) and pure tone (3 ms, 1 ms ramp) acoustic stimuli worn recorded with sub-dermal silver wire electrodes at the ear, the vertex and the back of the animal. After amplification (×100,000) the signals were averaged for 64-256 repetitions at each sound pressure presented (0-100 dB SPL in steps of 5 dB). The threshold was determined by the lowest sound pressure that produced potentials visually distinct from noise level. ABR measure points were just before noise respectively sham trauma, right after treatment, 1, 2,7 and 15 days post treatment.

Results

Real-time PCR for KCC2 from cochlear tissue sampled 15 days following treatment shows no difference in sham exposed ears (Group B), regardless of whether they were treated with AP or bumetanide. However, in noise exposed ears (Group A), a statistically significant down-regulation of KCC2 was observed in AP treated ears compared with those that were only sham exposed (2 sided Student t-test $p<0.05$), but not in bumetanide treated ears. KCC2 expression in noise exposed, bumetanide treated ears was similar to the level in sham exposed ears, but statistically significantly different from noise exposed, AP treated ears ($p<0.01$) (see FIG. 3a).

Figure 3:
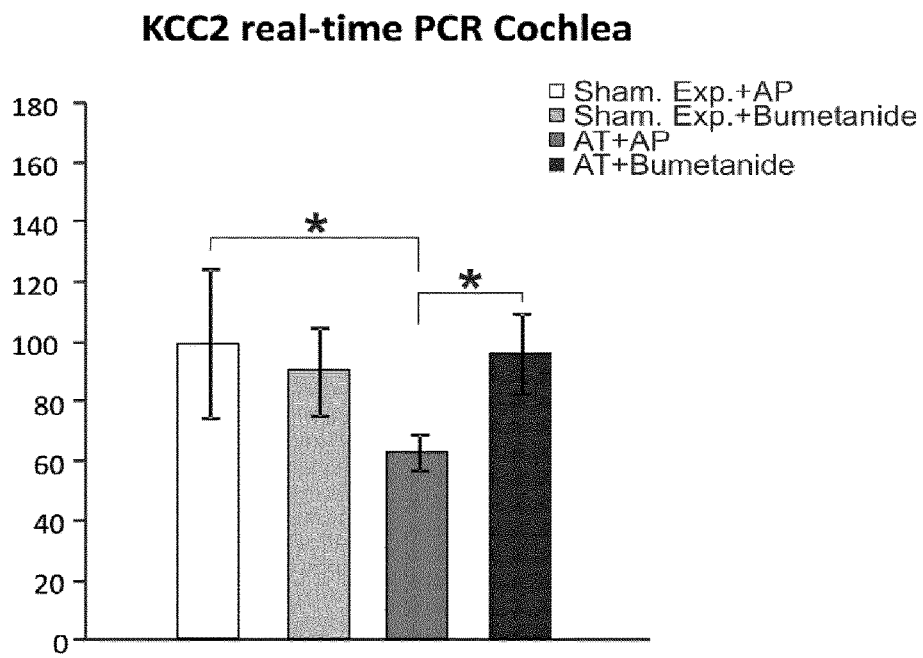
FIG. 3 shows that local administration of the NKCC1 inhibitor bumetanide to rat cochleae exposed to noise trauma protects from down-regulation of KCC2 and attenuates the morphological correlate of tinnitus.
- A) Real-time PCR for KCC2 expression in cochlear tissue 2 weeks following noise (black bar) or sham exposure (light grey bar) and treatment of rat cochleae by AP or bumetanide. Sham exposed cochleae treated with artificial perilymph (AP) served as control (white bar). 185 tRNA and β-actin were used as housekeeping genes. A statistically significant down-regulation of KCC2 was observed in noise exposed animals treated with AP. No such down-regulation of KCC2 was seen in sham or noise exposed animals treated with bumetanide. There was also a statistically significant difference in KCC2 expression between noise exposed animals treated with AP or bumetanide.
- Count of inner hair cell ribbon synapses 2 weeks following noise or sham exposure of rat cochlea. The number of ribbons per inner hair cell (IHC) is shown. Among those ears treated with AP, a significant decrease of ribbons was observed in noise exposed ears in the midbasal (middle columns) and basal (right columns) cochlear turns in comparison to sham exposed animals. In contrast, the decline in noise exposed ears that received bumetanide (black bar) was not significant in comparison to sham exposed animals (light grey bar). But there was a significant difference in ribbon numbers between noise exposed ears treated with AP (dark grey bar) or bumetanide (black bar). Apical turns (left) did not show much change as inner hair cells there are hardly affected by high-frequency trauma.
Figure 3:
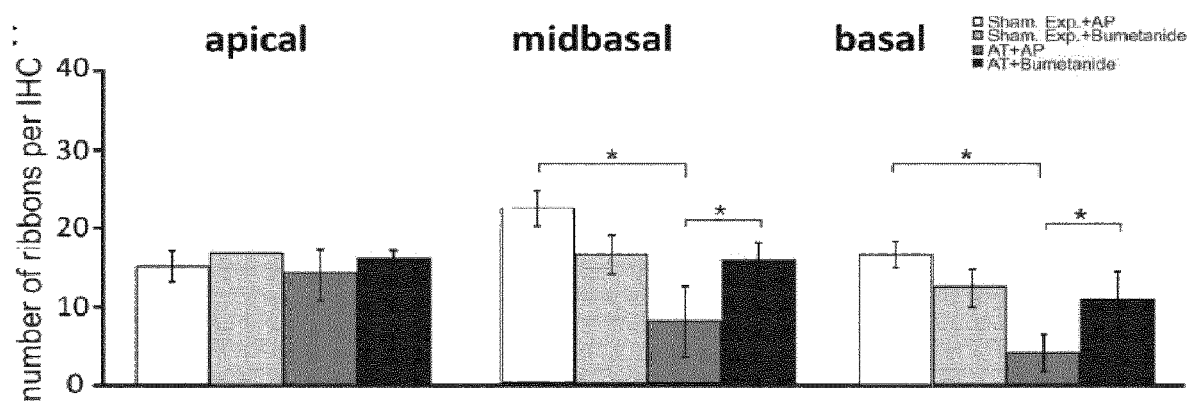

A surprisingly similar outcome was observed when counting ribbon synapses of inner hair cells (see FIG. 3b). Among those ears treated with AP, a significant decrease of ribbons was observed in noise exposed ears in the midbasal and basal cochlear turns in comparison to sham exposed animals ($p<0.01$). In contrast, the decline to noise exposed ears that received bumetanide was not significant in comparison to sham exposed animals. But there was a significant difference in ribbon numbers between noise exposed ear's treated with AP or bumetanide ($p<0.02$). Apical turns did not show much change as inner hair cells there are hardly affected by high-frequency trauma.

In summary, these results show for the first time ever that pharmacological modulation of the intracellular Cl⁻ concentration in inner hair cells is feasible and that up-regulation of KCC2 expression in inner hair cells can be achieved by inhibiting NKCC1. Such inhibition is exerted by NKCC1 antagonists which however, do not exert any direct effect on the increase of the KCC2 activity or expression. Rather, the effect is mediated by NKCC1 inhibition, which—as such—exerts an influence on the KCC2 activity or expression, namely an increase. Application of the NKCC1 inhibitor bumetanide results in a reduced loss of inner hair cell ribbons. As a biomarker for the presence of tinnitus this shows that this therapeutic strategy allows for attenuation, respectively suppression of tinnitus.

LITERATURE

Asiedu M, Ossipov M H, Kaila K, Price T J (2010), Acetazolamide and midazolam act synergistically to inhibit neuropathic pain, Pain 148(2); 302-308.

Balakrishnan V, Becker M, Löhrke H G, Güresir E, Friauf E (2003), Expression and function of chloride transporters during development of inhibitory neurotransmission in the auditory brainstem, Journal of Neuroscience 23: 4134-4145.

Blaesse P, Guillemin I, Schindler J, Schweizer M, Delpire E, Khiroug L, Friauf E, Nothwang H G (2006), Oligomerization of KCC2 correlates with development of inhibitory neuro-transmission, Journal of Neuroscience 26(41): 10407-10419.

Blaesse P, Airaksinen, Rivera C, Kaila K (2009), Cation-chloride co-transporters and neuronal function, Neuron 61, 820-838.

Coull J, Beggs S, Boudreau D, Boivin D, Tsuda M, Inoue K, Gravel C, Salter M W, De Koninck Y (2005), BDNF from microglia causes the shift in neuronal anion gradient underlying neuropathic pain, Nature 438(7070): 1017-1021

Dobie R (2004b), Clinical trials and drug therapy for tinnitus, in: Tinnitus—theory and management, Snow J B (ed.), B C Decker, Hamilton—London: 266-277.

Eggermont J J, Roberts L E (2004), The neuroscience of tinnitus, Trends in Neurosciences 27(11), 676-682.

Estévez R, Boettger T, Stein V, Birkenhäger R, Otto E, Hildebrandt F, Jentsch T J (2001), Barttin is a Cl⁻channel beta-subunit crucial for renal Cl⁻reabsorption and inner ear K⁺secretion. Nature 414(6863): 558-561.

Gagnon K B E, England R, Delpire E (2006), Characterization of SPAK and OSR1, regulatory kinases of the Na—K-2Cl Co-transporter, Molecular and Cellular Biology 26(2); 689-698.

Haas M (1994), The Na—K—Cl cotransporters, American Journal of Physiology 267: C869-C885.

Huberfeld G, Wittner L, Clemenceau S, Baulac M, Kaila K, Miles R, Rivera C (2007), Perturbed chloride homeostasis and GABAergic signaling in human temporal lobe epilepsy, Journal of Neuroscience 27(37): 9866-9673.

Kahle K T, Rinehart J, de Los Heros P, Louvi A, Meade P, Vazquez N, Hebert S C, Gamba G, Gimenez I, Lifton R P (2005), WNK3 modulates transport of Cl- in and out of cells; implications for control of cell volume and neuronal excitability, Proc. Natl. Acad. Sci. USA 102(46); 16783-16788.

Langguth B, Salvi R, Elgoyhen A B (2009), Emerging pharmacotherapy of tinnitus, Expert Opinion on Emerging Drugs, 15(7-8); 300-305.

Lauf P K, Adragna N C (2000), K—Cl cotransport: properties and molecular mechanism, Cell Physiol Biochem. 10(5-6): 341-354.

Lee H H, Walker J A, Williams J R, Goodier R J, Payne J A, Moss S J (2007), Direct protein kinase C-dependent phosphorylation regulates the cell surface stability and activity of the potassium chloride co-transporter KCC2, Journal of Biologic Chemistry 282(41): 29777-29784.

Lenart B, Kintner D B, Shull G E, Sun D (2004), Na—K—Cl cotransporter-mediated intracellular Na+ accumulation affects Ca2+ signaling in astrocytes in an in vitro ischemic model, Journal of Neuroscience 24(43): 9585-9597.

Menkes D B, Larson P M (1998), Sodium valproate for tinnitus, Journal of Neurology, Neurosurgery and Psychiatry 65(5): 803.

Okarnura H O, Sugai N, Suzuki K, Ohtani I (1996), Enzyme-histochemical localization of carbonic anhydrase in the inner ear of the guinea pig and several improvements of the technique, Histochemisty and Cell Biology 106(4): 425-430.

Panford-Walsh R, Singer W, Rüttiger L, Hadjab S, Tan J, Geisler H S, Zimmermann U, Köpschall I, Rohbock K, Vieljans A, Oestreicher E, Knipper M (2008), Midazolam reverses salicylate-induced changes in brain-derived neurotrophic factor and arg3.1 expression: implications for tinnitus perception and auditory-plasticity, Molecular Pharmacology 74(3): 595-604.

Payne J A (1997), Functional characterization of the neuronal-specific K—Cl co-transporter: implications for [K+]o regulation, American Journal of Physiology 273(5 Pt 1): C1516-1525.

Payne J A, Rivera C, Volpio J, Kaila K (2003), Cation-chloride co-transporters in neuronal communication, development and trauma, Trends in Neurosciences 26(4): 199-206.

Piccirillo J F, Finnell J, Vlahiotis A, Chole R A, Spitznagel E (2007), Relief of idiopathic subjective tinnitus: is gabapentin effective? Archives of Otolaryngology—Head & Neck Surgery 133(4): 390-397.

Rivera C, Li H, Thomas-Crusells J, Lahtinen H, Viitanen T, Nanobashvilli A, Kokaia Z, Airaksinen M S, Voipio J, Kaila K, Saarma M (2002), BDNF-induced TrkB activation down-regulates the K+-Clco-transporter KCC2 and impairs neuronal Cl-extrusion, Journal of Cell Biology 159(5): 747-752.

Risey J A, Guth P S, Amedee R G (1995), Furosemide distinguishes central and peripheral tinnitus, International Tinnitus Journal 1: 99-103.

Rü-tiger L, Ciuffani J, Zenner H P, Knipper M (2003), A behavioral paradigm to judge acute sodium salicylate-induced sound experience in rats: a new approach for an animal model on tinnitus. Hearing Research 180(1-2): 39-50.

Shulman A, Strashun A, Goldstein B (2002), GABAA-benzodiazepine-chloride receptor-targeted therapy for tinnitus control: preliminary report, International Tinnitus Journal 8; 30-36.

Staley K J (2002), Diuretics as antiepileptic drugs: should we go with the flow?, Epilepsy Currents 2(2): 35-38.

Tan J, Rüttiger L, Panford-Walsh R, Singer W, Schulze H, Kilian S B, Hadjab S, Zimmermann U, Köpschall I, Rohbock K, Knipper M (2007), Tinnitus behavior and hearing function correlate with the reciprocal expression patterns of BDNF and Arg3 .I/are in auditory neurons following acoustic trauma, Journal of Neuroscience 145; 715-726.

Vale C, Caminos E, Martinez-Galán J R, Juiz J M (2005), Expression and developmental regulation of the K+-Cl-co-transporter KCC2 in the cochlear nucleus, Hearing Research 206(1-2): 107-115.

Verdel B M, van Puijenbroek E P, Souverein P C, Leufkens H G, Egberts A C (2008), Drug-related nephrotoxic and ototoxic reactions: a link through a predictive mechanistic commonality, Drug Safety 31 (10): 877-884.

Wangemann P (2008), Cochlear homeostasis and homeostatic disorders, in: Auditory trauma, protection, and repair, Schacht J, Popper A N, Ray R R (eds.), Springer Handbook of Auditory Research 31, Springer, New York: 49-100.

Wenz M, Hartmann A M, Friauf E, Nothwang H G (2009), CIP1 is an activator of the K+-Cl-co-transporter KCC2, Biochemical and Biophysical Research Communications 381 (3): 388-392.

Westerberg B D, Roberson J B, Stach B A (1996), A double-blind placebo-controlled trial of baclofen in the treatment of tinnitus, American Journal of Otology 17(6): 896-903.

Yang K, Huang Z W, Huang J, Zhang X J, Xiao B K (2008), Expression of the neuron-specific potassium chloride co-transporter KCC2 in adult rat cochlea, Neuroscience Letters 441(2): 205-209.

Zhang D, Gopalakrishnan S M, Freiberg G, Surowy C S (2010), A thallium transport FLIPR-based assay for the identification of KCC2-positive modulators, Journal of Bimolecular Screening 15(2): 177-184.

The invention claimed is:

1. A method for treating tinnitus in a subject in need thereof comprising systemically administering to the subject an oral pharmaceutical composition comprising a therapeutically effective amount of a compound, wherein the compound is:

a compound according to formula II or formula III below:

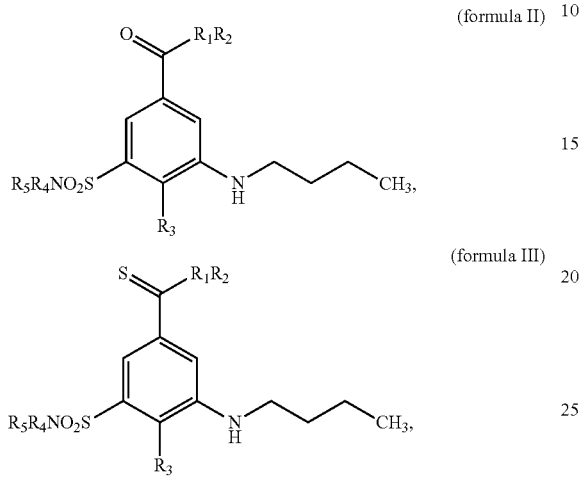

or an isomer or enantiomer thereof,
or a pharmaceutically acceptable salt, solvate, tautomer or hydrate thereof, wherein
$R_1$ is not present, H, O or S;
$R_2$ is not present, H or when $R_1$ is O or S, $R_2$ is selected from the group consisting of hydrogen, alkyl, aralkyl, aryl, alkylaminodialkyl, alkylcarbonylaminodialkyl, alkyloxycarbonylalkyl, alkylcarbonyloxyalkyl, alkylaldehyde, alkylketoalkyl, alkylamide, alkarylamide, arylamide, an alkylammonium group, alkylcarboxylic acid, alkylheteroaryl, alkylhydroxy, a biocompatible polymer such as alkyloxy(polyalkyloxy)alkylhydroxyl, a polyethylene glycol (PEG), a polyethylene glycol ester (PEG ester) and a polyethylene glycol ether (PEG ether), methyloxyalkyl, methyloxyalkaryl, methylthioalkyl and methylthioalkaryl, unsubstituted or substituted, and when $R_1$ is not present, $R_2$ is selected from the group consisting of hydrogen, N,N-dialkylamino, N,N-dialkarylamino, N,N-diarylamino, N-alkyl-N-alkarylamino, N-alkyl-N-arylamino, N-alkaryl-N-arylamino, unsubstituted or substituted;
$R_3$ is selected from the group consisting of aryl, halo, hydroxy, alkoxy, and aryloxy, unsubstituted or substituted; and
$R_4$ and $R_5$ are each independently selected from the group consisting, of hydrogen, alkylaminodialkyl, carbonylalkyl, carbonylalkaryl, carbonylaryl, and salts thereof such as sodium, potassium, calcium, ammonium, trialkylarylammonium and tetraalkylammonium salts.

2. The method of claim 1, wherein the therapeutically effective amount of the compound is an amount sufficient to increase activity and/or expression of KCC2 in auditory sensorineural structures in the subject.

3. The method of claim 1, wherein the compound is selected from sulfonamides.

4. The method of claim 1, wherein the compound is bumetanide or an analog thereof.

5. The method of claim 1, wherein the sulfonamide compound is a bumetanide.

6. The method of claim 4, wherein the sulfonamide compound is selected from the group consisting of
(i) bumetanide, bumetanide aldehyde, bumetanide methyl ester, bumetanide cyanomethyl ester, bumetanide ethyl ester, bumetanide isoamyl ester, bumetanide octyl ester, bumetanide benzyl ester, bumetanide dibenzylamide, bumetanide diethylamide, bumetanide morpholinoethyl ester, bumetanide 3-(dimethylaminopropyl) ester, bumetanide N,N-diethylglycolamido ester, bumetanide N,N- dimethylglycolamido ester, bumetanide pivaxetil ester, bumetanide propaxetil ester, bumetanide methoxy(polyethyleneoxy)$_{n-1}$-ethyl ester, bumetanide benzyltrimethylammonium salt and bumetanide cetyltrimethylammonium salt, bumetanide [-(C=O)-SH] thioacid, bumetanide S-methyl thioester, bumetanide S-cyanomethyl thioester, bumetanide S-ethyl thioester, bumetanide S-isoamyl thioester, bumetanide S-octyl thioester, bumetanide S-benzyl thioester, bumetanide S-(morpholinoethyl) thioester, bumetanide S-[3-(dimethylaminopropyl)] thioester, bumetanide S-(N,N-diethylglycolamido) thioester, bumetanide S-(N,N-dimethylglycolamido) thioester, bumetanide S-pivaxetil thioester, bumetanide S-propaxetil thioester, bumetanide S-[methoxy(polyethyleneoxy)$_{n-1}$-ethyl] thioester, bumetanide [-(C=O)-S$^-$] benzyltrimethylammonium thioacid salt and bumetanide [-(C=O)-S$^-$] cetyltrimethylammonium thioacid salt, metastable bumetanide [-(C=S)-OH] thioacid, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl) thioester, bumetanide O-[3-(dimethylaminopropyl)] thioester, bumetanide O-(N,N- diethylglycolamido) thioester, bumetanide, O-(N,N-dimethylglycolamido) thioester, bumetanide O-pivaxetil thioester, bumetanide O-propaxetil thioester, bumetanide O-[methoxy(polyethyleneoxy)$_{n-1}$-ethyl] thioester, bumetanide [-(C=S)-O$^-$] benzyltrimethyl-ammonium thioacid salt and bumetanide [-(C=S)-O$^-$] cetyltrimethylammonium thioacid salt, bumetanide thioaldehyde, bumetanide [-(C=S)-SH] dithioacid, bumetanide methyl dithioester, bumetanide cyanomethyl dithioester, bumetanide ethyl dithioester, bumetanide isoamyl dithioester, bumetanide octyl dithioester, bumetanide benzyl dithioester, bumetanide dibenzylthioamide, bumetanide diethylthioamide, bumetanide morpholinoethyl dithioester, bumetanide 3-(dimethylaminopropyl) dithioester, bumetanide N,N-diethylglycolamido dithioester, bumetanide N,N-dimethylglycolamido dithioester, bumetanide pivaxetil dithioester, bumetanide propaxetil dithioester, bumetanide methoxy(polyethyleneoxy)$_{n-1}$-ethyl dithioester, bumetanide benzyltrimethylammonium dithioacid salt and bumetanide cetyltrimethyl-ammonium dithioacid salt.

7. The method of claim 1, further comprising administering to the subject one or more carbonic anhydrase inhibitors selected from acetazomalide, dichlorphenamide, dorzolamide, brinzolamide and/or methazolamide.

8. The method of claim 1, further comprising administering to the subject one or more GABAergic agonists and/or one or more glycine agonists.

9. The method of claim 1, wherein the pharmaceutical composition is provided in a liquid, semi-liquid or viscous form.

10. The method of claim 1, wherein the pharmaceutical composition contains a biodegradable polymer selected from the group consisting of hyaluronic acid, hyaluronates, lecithin gels, (poly)alanine derivatives, pluronics, poly(ethyleneglycol), poloxamers, chitosans, xyloglucans, collagens, fibrins, polyesters, poly(lactides), poly(glycolide), poly(lactic-co-glycolic acid) copolymer, sucrose acetate isobutyrate, and glycerol monooleate.

11. The method of claim 1, wherein the compound antagonizes the function of NKCC1 by decreasing or inhibiting its activity and/or expression.

12. The method of claim 1, wherein the compound decreases activity and/or expression of NKCC1 and increases activity and/or expression of KCC2.

13. The method of claim 1, wherein the compound is selected from the group consisting of bumetanide morpholinoethyl ester, bumetanide diethylamide and bumetanide cetyltrimethylammonium salt.

14. The method of claim 1, wherein the pharmaceutical composition is provided in a gel-like form.

* * * * *

UNITED STATES PATENT AND TRADEMARK OFFICE
CERTIFICATE OF CORRECTION

PATENT NO. : 10,709,682 B2
APPLICATION NO. : 15/869929
DATED : July 14, 2020
INVENTOR(S) : Marlies Knipper-Breer et al.

It is certified that error appears in the above-identified patent and that said Letters Patent is hereby corrected as shown below:

On the Title Page

Item (72) Inventors:
"Luckas Ruettiger" should read -- Lukas Ruettiger --

Signed and Sealed this
Twenty-ninth Day of September, 2020

Andrei Iancu
*Director of the United States Patent and Trademark Office*